United States Patent
Ilan et al.

(10) Patent No.: US 12,364,785 B2
(45) Date of Patent: Jul. 22, 2025

(54) EXPANDABLE HEMOSTAT COMPOSED OF OXIDIZED CELLULOSE

(71) Applicant: Ethicon, Inc., Raritan, NJ (US)

(72) Inventors: Erez Ilan, Kibbutz Netzer Sereni (IL); Omri Faingold, Rehovot (IL); Tamar Auerbach-Nevo, Rehovot (IL); Tali Negreanu-Gilboa, Givatayim (IL); Hadas Alperin, Tel-Aviv (IL); Yi-Lan Allen Wang, Belle Mead, NJ (US); Dwayne Looney, Flemington, NJ (US)

(73) Assignee: Ethicon, Inc., Raritan, NJ (US)

(*) Notice: Subject to any disclaimer, the term of this patent is extended or adjusted under 35 U.S.C. 154(b) by 598 days.

(21) Appl. No.: 16/945,990

(22) Filed: Aug. 3, 2020

(65) Prior Publication Data

US 2021/0038757 A1    Feb. 11, 2021

Related U.S. Application Data

(60) Provisional application No. 62/883,764, filed on Aug. 7, 2019.

(51) Int. Cl.
| | | |
|---|---|---|
| *A61L 15/28* | (2006.01) | |
| *A61L 15/42* | (2006.01) | |
| *A61L 15/44* | (2006.01) | |
| *A61L 15/64* | (2006.01) | |
| *C08L 1/04* | (2006.01) | |

(52) U.S. Cl.
CPC ............. *A61L 15/28* (2013.01); *A61L 15/425* (2013.01); *A61L 15/44* (2013.01); *A61L 15/64* (2013.01)

(58) Field of Classification Search
CPC ........ A61L 15/28; A61L 15/42; A61L 15/425; A61L 15/44; A61L 15/64; A61L 2400/04; C08L 1/04; B60T 2220/04; B60T 7/042; B60W 10/18; B60W 2510/0647; B60W 2520/10; B60W 2530/10; B60W 2530/16; B60W 2540/12; B60W 2552/15; B60W 2720/10; B60W 40/105; B60W 40/13; B60W 50/14

See application file for complete search history.

(56) References Cited

U.S. PATENT DOCUMENTS

| | | | |
|---|---|---|---|
| 3,364,200 A | 1/1968 | Ashton et al. | |
| 4,045,238 A | 8/1977 | Battista et al. | |
| 5,180,398 A | 1/1993 | Boardman et al. | |
| 7,279,177 B2 | 10/2007 | Looney et al. | |
| 7,666,803 B2 | 2/2010 | Shetty et al. | |
| 8,329,211 B2 | 12/2012 | Moloye-olabisi et al. | |
| 8,518,064 B2 | 8/2013 | Kurrus et al. | |
| 8,709,463 B2 | 4/2014 | Looney et al. | |
| 8,815,832 B2 | 8/2014 | Wang et al. | |
| 8,828,050 B2 | 9/2014 | Gregory et al. | |
| 10,034,957 B2 | 7/2018 | Wang | |
| 11,986,489 B2* | 5/2024 | Galloway | A61L 15/28 |
| 2004/0005350 A1 | 1/2004 | Looney et al. | |
| 2004/0120993 A1 | 6/2004 | Zhang | |
| 2004/0193088 A1* | 9/2004 | Looney | A61L 15/425 602/48 |
| 2005/0287215 A1* | 12/2005 | Looney | A61L 15/425 424/485 |
| 2006/0078589 A1 | 4/2006 | Jensen et al. | |
| 2007/0014862 A1* | 1/2007 | Pameijer | A61L 15/28 424/488 |
| 2008/0027365 A1 | 1/2008 | Huey | |
| 2012/0101520 A1 | 4/2012 | Ginn et al. | |
| 2014/0142523 A1 | 5/2014 | Steinbaugh et al. | |
| 2017/0042930 A1* | 2/2017 | Galloway | A61K 31/717 |
| 2018/0036414 A1 | 2/2018 | Kim et al. | |

FOREIGN PATENT DOCUMENTS

| | | |
|---|---|---|
| CN | 1509768 | 7/2004 |
| CN | 1531976 A | 9/2004 |
| CN | 107580494 | 1/2018 |
| CN | 108348633 A | 7/2018 |
| EP | 1802358 A2 | 7/2007 |
| JP | 2012122187 A | 6/2012 |
| JP | 2015517388 A | 6/2012 |
| JP | 2013526369 A | 6/2013 |
| WO | 2013096176 A1 | 6/2013 |

OTHER PUBLICATIONS

Duncan; "Headspace Moisture Analysis for Determination of Residual MoistureContent in Lyophilized Pharmaceutical Products"; BioPharm International; vol. 29, Issue 6; pp. 36-40. Published on Mar. 31, 2016.*
International Search Report dated Oct. 8, 2020 for Application No. PCT/IB2020/057322.
International Preliminary Report, dated Feb. 8, 2022 for Application No. PCT/IB2020/057322, pp. 1-9.
International Preliminary Report and Written Opinion, PCT/IB2020/057322, Feb. 8, 2022, pp. 1-9.

* cited by examiner

*Primary Examiner* — Jeffrey T. Palenik
(74) *Attorney, Agent, or Firm* — David R. Crichton

(57) ABSTRACT

An expandable biodegradable hemostatic matrix comprised of oxidized cellulose, and having a density ranging from about 0.8 to about 1.2 gr/cm³ is disclosed herein. The matrix may be expandable to at least 3 times its original volume within 4 sec upon contact with an aqueous solution room temperature. Further disclosed are methods for making the hemostatic matrix as well as method of treating a wound.

13 Claims, 10 Drawing Sheets

EXPANDABLE HEMOSTAT COMPOSED OF OXIDIZED CELLULOSE

FIELD OF THE INVENTION

The present invention relates, inter alia, to expandable biodegradable hemostatic matrix of oxidized cellulose (OC) and uses thereof e.g., for treating a wound.

BACKGROUND OF THE INVENTION

In a wide variety of circumstances, animals, including humans, can suffer from bleeding due to wounds or during surgical procedures. In some circumstances, the bleeding is relatively minor and normal blood clotting functions, so the application of simple first aid is all that is required. In other circumstances substantial bleeding can occur. These situations usually require specialized equipment and materials as well as personnel trained to administer appropriate aid.

Conventional methods to achieve hemostasis include the use of surgical techniques, sutures, ligatures or clips, and energy-based coagulation or cauterization. When these conventional measures are ineffective or impractical, adjunctive hemostasis techniques and products are required.

The selection of appropriate methods or products for the control of bleeding is dependent upon many factors, which include but are not limited to bleeding severity, anatomical location of the source and the proximity of adjacent critical structures, whether the bleeding is from a discrete source or from a broader surface area, visibility and precise identification of the source and access to the source.

In an effort to address the above-described problems, materials have been developed for controlling excessive bleeding. Topical Absorbable Hemostats (TAHs) are widely used in surgical applications. TAHs encompass products based on oxidized cellulose (OC), gelatin, collagen, chitin, chitosan, etc. To improve the hemostatic performance, scaffolds based on the above materials can be combined with biologically-derived clotting factors, such as thrombin and fibrinogen.

Due to its biodegradability, and its bactericidal and hemostatic properties, oxidized cellulose (OC)-based materials, such as oxidized regenerated cellulose (ORC), have long been used as topical hemostats in a variety of surgical procedures, including neurosurgery, abdominal surgery, cardiovascular surgery, thoracic surgery, head and neck surgery, pelvic surgery and skin and subcutaneous tissue procedures. Several methods for forming various types of hemostats based on OC materials are known, whether made in powder, woven, non-woven, knit, and other forms. Currently utilized hemostats include powder, or fabrics comprising ORC.

Fast management of rapid bleeding is crucial for surgical procedures. Hemostasis can be achieved by a variety of methods. A common practice is the use of manual compression in which pressure is applied on the wound through a bandage or a hemostatic patch to facilitate the formation of a clot. Manual compression has some notable disadvantages: it is considerably cumbersome and relatively time consuming for the surgical staff. Regarding its application, manual compression is not effective in cases in which blood is lost from narrow and hard-to-reach spaces, gaps, or cavities. In such cases, a flowable sealant is commonly applied through a conducting applicator that is used to achieve hemostasis. A line of flowable sealant products are available in the market, most of them are based on biologically active components.

Biological hemostats carry a potential risk of contamination and their costs are high. Further, several hemostats in the market require laborious preparation before applying, a degree of expertise from the surgical staff and they lack the required efficacy in cases of rapid blood loss.

U.S. Patent Application having Publication No. 2012/0101520 relates to apparatus and methods used to seal a vascular puncture site, particularly sites of punctures that are the result of catheterization or other interventional procedures. The sealing device includes a sealing member and a tether. The sealing member occupies a space in an incision, puncture, or other wound and sealing the space that it occupies, to prevent further blood flow. The tether is attached to the sealing member, and provides the user with the ability to withdraw the sealing member if necessary.

U.S. Pat. No. 8,518,064 relates generally to a method for anchoring an expandable biocompatible plug material to a vessel wall to form an anchored occluding plug blocking or reducing blood flow to a desired vessel target, such as an artery supplying blood to a neoplastic tissue or tumor.

U.S. Patent Application having Publication No. 2005/0287215 discloses a plurality of packed particles that contain interstitial pores, where the interstitial pores have a pore volume and a median pore diameter effective to provide improved absorption of physiological fluids or an aqueous media when placed in contact therewith, compared to a plurality of unpacked particles of the same material, where the particles are made of a biocompatible material and have an average diameter suitable for use in providing hemostasis to a site of a body of a mammal requiring hemostasis, hemostatic compositions containing such plurality of packed particles, methods of making such particles and compositions and medical devices suitable for delivering and containing the hemostatic plurality of particles and/or composition to a site of a body.

U.S. Patent Application having Publication No. 2014/0142523 discloses, inter alia, self-expanding wound dressings that include a first outer layer, a second outer layer, and a liquid-expandable layer disposed between the first outer layer and the second outer layer, wherein the liquid-expandable layer includes a plurality of liquid-expandable articles retained by a substrate, wherein the plurality of liquid-expandable articles expand to form expanded articles upon contact with a liquid.

U.S. Pat. No. 8,828,050 relates to hemostatic composition comprising a plurality of liquid expandable articles capable of expanding upon contact with a liquid. A suitable composition comprises a plurality of liquid-expandable articles that may be mechanically uncoupled from one another and therefore may be capable of moving independently from one another. The plurality of liquid-expandable articles may comprise a compressed material capable of a high-degree of expansion upon liquid contact.

U.S. Patent Application having Publication No. 2007/0014862 discloses, inter alia, a hemostatic agent comprising oxidized cellulose in the form of a compressible, shapeable mass that can remain substantially in the compressed or shaped form for placement on a bleed site or into a wound gap. The oxidized cellulose may be a pellet of unwoven oxidized cellulose fibrous strands, or it may be strands of unwoven cellulose fibers woven or otherwise arranged into a gauze or mesh. The pellet may be compressed before being applied to the wound, which thereby allows the pellet to expand to conform to the shape of the wound gap. The pellet may be allowed to remain in the wound gap during the healing of the wound, thus causing the pellet to be absorbed by the biological processes of the body.

U.S. Patent Application having Publication No. 2006/0078589 discloses a device for treating oral wounds that form a gap and hence too large to suture. The device is intended to fill the resulting wound gap and upon contact with bleeding tissues cause local hemostasis. The device will remain in and protect the wound gap during the healing process.

However, since control of bleeding is essential and critical in surgical procedures to minimize blood loss, to reduce post-surgical complications, and to shorten the duration of the surgery in the operating room, there is a need of improved hemostatic forms and materials which facilitate ease of application, especially in hard-to-reach bleeding sites.

SUMMARY OF THE INVENTION

The invention relates, inter alia, to an expandable hemostat matrix constructed from compressed oxidized cellulose (OC) such as oxidized regenerated cellulose (ORC), which may be used e.g., for achieving hemostasis in case of a puncture wound or a tissue gap. The hemostatic oxidized cellulose material can rapidly expand when exposed to body fluid, and following absorption with blood, the disclosed matrix can reduce the bleeding without further applying external compression, and may take on the shape of the wound site enabling hemostasis. The matrix may be left at the wound site as it dissolves over time. The matrix may be produced from the compression of different textured OC or ORC material (for example, non-woven, and knitted).

The common practice of manual compression is considerably cumbersome and relatively time consuming for the surgical staff the common practice, and is not effective in cases in which blood is lost from narrow and hard-to-reach spaces.

In sharp distinction, the disclosed expandable matrix may be effective as an immediate solution for treating blood loss injuries in which manual compression is not feasible or effective. Thus, the matrix allows to overcome the disadvantages of common practice of manual compression in which pressure is applied on the wound through a bandage or a hemostatic patch to facilitate the formation of a clot.

The matrix has further notable advantages over existing solutions: not requiring preparation time, stable at room temperature (RT), cost-effective and safety over biological hemostats.

In the Examples section below it is further demonstrated that the disclosed matrix comprising ORC non-woven material exhibits superior expansion characteristics and hemostasis efficacy as compared to a tablet composed of an ORC knitted source material and powder.

Accordingly, the expandable matrix is also effective as an immediate solution for treating blood loss injuries, for example, for dental procedures with strong bleeding. Furthermore, to acting as an efficient hemostat, ORC is a bactericidal compound, which is advantageously following an intervention in a body cavity, such as the mouth which holds a high concentration of bacteria.

According to an aspect of the present invention, there is provided a biodegradable hemostatic matrix comprising oxidized cellulose (OC), wherein said matrix: (i) has a density ranging from about 0.8 to about 1.2 gr/cm$^3$, and (ii) is expandable to at least 3 times, least 4 times, or least 5 times its original volume within 4 sec upon contact with an aqueous solution at at-least one temperature between 10 and 40° C. In some embodiments, the matrix has a density of about 1.2 gr/cm$^3$.

In some embodiments, the OC in the matrix comprises or is in the form of one or more sheets, e.g., fibrous and/or packed layered sheets.

In some embodiments, the matrix has a volume greater than 5 mm$^3$, e.g., 0.3 to 0.9 cm$^3$.

In some embodiments, the matrix is in a compressed form. In some embodiments, the matrix is in the pre-expanded state or form.

The term "compressed" may refer to being compressed in one or more directions, e.g., by horizontal, vertical and/or radial compressive forces.

In some embodiments, the matrix is substantially in a cylindrical, rectangular, and/or polygonal shape.

In some embodiments, the matrix is capable of expanding to at least 90% of its maximum expansion capacity within 30 seconds following immersion in an aqueous solution, and is expandable to 3 to 30, or 15 to 30 times its original volume within 4 sec upon contact with an aqueous solution at at-least one temperature between 10 and 30° C.

In some embodiments, the matrix is in the form of an article selected from a tablet and a wound dressing.

In some embodiments, the matrix the OC comprises oxidized regenerated cellulose (ORC).

In some embodiments, the OC matrix originates from an OC- (or ORC-) based material having the form selected from: knitted fabric, non-woven fabric, woven fabric, a shredded material, and any combination thereof.

In some embodiments, the ORC-based material is in the form of a non-woven fabric.

In some embodiments, the matrix further comprises one or more additives selected from calcium salt, anti-infective agent, and hemostasis promoting agent.

In some embodiments, the matrix further comprises one or more excipients selected from sodium chloride, mannitol, albumin, and sodium acetate.

In some embodiments, the carboxyl content of the OC ranges from 12% to 21%, by weight, per United States Pharmacopeia (USP) 23-NF18.

In some embodiments, the matrix in the pre-expansion form has a total surface area ranging from about 3 to about 5 cm$^2$.

In some embodiments, the matrix has a pre-expansion volume ranging from about 0.4 to about 0.8 cm$^3$.

In some embodiments, the matrix is for use in controlling bleeding in soft tissues.

In some embodiments, the matrix is for use in inhibiting or reducing the formation of load of a microorganism.

In some embodiments, the matrix is produced by compressing an OC-based material by applying on at least one surface thereof a pressure ranging from 0.3 to 7 ton/cm$^2$, e.g., 0.3 to 2.5 ton/cm$^2$.

According to an aspect of the present invention, there is provided a method of making the hemostatic matrix in any embodiment thereof, the method comprising the step of compressing an OC-based material by applying on at least one surface thereof a pressure ranging from about 0.3 to about 7 ton/cm$^2$.

In some embodiments of the method of making the hemostatic matrix, the OC material comprises ORC.

In some embodiments of the method of making the hemostatic matrix, the ORC is in the non-woven form.

In some embodiments of the method of making the hemostatic matrix, the method further comprises the step of mixing the OC material with one or more additives selected from calcium salt, anti-infective agent, and hemostasis promoting agent.

According to an aspect of the present invention, there is provided a method of treating a wound comprising the step of applying the disclosed biodegradable hemostatic matrix of any embodiment thereof onto and/or into the wound of a subject in a need thereof.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

DESCRIPTION OF EMBODIMENTS OF THE INVENTION

Figure 1B:
FIGS. 1A-1B present photographs showing the disclosed matrix in the form of a pellet, with different sizes; large (FIG. 1A), and small (FIG. 1B); numbers in rulers are in centimeters.

An object of the present invention is to provide a hemostat matrix composition comprising oxidized cellulose (OC) e.g., oxidized regenerated cellulose (ORC) having a certain range of density, capable of high-degree of expansion upon contact with body fluids, which may easily be applied to a site of need e.g., for achieving hemostasis in case of a puncture wound or a tissue gap. An advantage of the expandable composition as described herein is the ability to quickly expand into expanded form. This allows the expanded composition to quickly fill the wound cavity and provide a nearly immediate hemostatic effect without the need for applying any external pressure or compression. Additional advantages associated with the present invention include, inter alia, improved positioning within the wound, improved tissue apposition and better conformation to intricate wound contours.

As explained in more detail below, the disclosed composition can be applied to a bleeding tissue and thereafter can rapidly expand upon exposing to body fluid, while taking on the shape of the wound site, enabling to assist in hemostasis. The composition can be left at the wound site as it degrades over time.

"Hemostasis" (or "haemostasis") refers to the first stage of wound healing. It is a process which causes bleeding to stop. By "assist in hemostasis" it is meant to help reduce or stop bleeding. By "applied to a bleeding tissue" it is meant to refer to a topical application of the composition at the bleeding site, e.g., at a surgical site to control bleeding. Control of bleeding is needed in various situations including treatment of wounds, or during surgical procedures, such as, for example, laparoscopic surgery, neurosurgery, abdominal surgery, cardiovascular surgery, thoracic surgery, head and neck surgery, pelvic surgery and skin and subcutaneous tissue procedures. For at least one of these situations, the composition of the invention may serve as a suitable sealant.

In some embodiments, the composition comprises compressed OC. In some embodiments, the OC is compressible.

The term "compressed", or "compressed state", refers to the state of a material subsequent to compression e.g., by applying a pressure thereon. Conversely, the term "uncompressed" refers to the state of a material prior to compression, or upon expansion e.g., subsequent to its degradation or explosion. The term "compressible" refers to the ability of a material to undergo compression.

In some embodiments, the composition, being in a dry state, remains substantially in the compressed or shaped form prior to contact or placement in/on aqueous media such as in a bleeding site or in a wound gap.

The term "compressed state" is also referred to herein as "original volume".

In some embodiments, the compressed material, upon exposure to liquid, e.g., an aqueous solution, may rapidly expand as described herein, without using exogenous gases or pressure. By "aqueous solution" it is meant to encompass both water as well as a solution in which the solvent is or comprises water, e.g., saline, and body fluids, such as blood. The water may refer to pure water.

The compressed matrix so formed exhibit improved expansion and/or liquid (e.g., water)-swellability when compared to particles, e.g., milled ORC particles. Compositions of the present invention may be applied as is in a bleeding site, or in some embodiments, be applied together with saline, simultaneously or sequentially. In some embodiments, the matrix may be applied manually, or, in some embodiments, using a device such as a medical device, e.g., trocar (of various dimensions e.g., a diameter of 5, 10, 12, 15 mm, including any value therebetween), or other known applicators. Depending on shape, form and size desired for the contemplated use, different molds or other compression techniques may be used to achieve the desired body of the disclosed matrices or compositions.

Embodiments of the present invention further relate, inter alia, to fast swelling, and superabsorbable, biodegradable hemostatic composition. The fast swelling may be provided upon contact with plasma, allowing the composition to absorb at least some, or even most of plasma components.

The term "absorb", or any inflection thereof, refers to the physical state in which the fluid (e.g., aqueous media such as body fluid) is distributed throughout the inner body of the OC matrix.

Upon contact and swelling, e.g., up to 2, 3, 4, 5, 6, 7, 8, 9, 10, or even to more than up to 20 times of the dry composition, the disclosed composition allows to fill up e.g., a confined wound space to simulate tamponade effect and enhance the natural clotting process. In some embodiments, the disclosed composition is flexible, thereby ensuring its access to narrow spaces and its application to uneven surfaces, making it a useful material to address the intra-operational bleeding or oozing. The instant matrix is particularly suitable for hard-to-access wounds such as tissue crevice or cavity bleeding.

By "dry" it is meant to refer to OC or ORC comprising less than 8%, less than 5%, or less than 1%, of water, by weight.

The term "flexible" in the context of the disclosed matrix (e.g., in the form of a tablet or pellet) pertains to a material which may be bent or rolled without breaking.

According to an aspect of the present disclosure, there is provided a biodegradable hemostatic matrix comprising oxidized cellulose (OC), wherein the matrix: (i) has a density ranging from about 0.8 to about 1.2 gr/cm$^3$, and (ii) is expandable to at least 3 times its original volume within 4 sec upon contact with an aqueous solution at at-least one temperature between 10 and 40° C.

In some embodiments, the matrix is in the form of an article selected from, without being limited thereto, a tablet and a pellet.

As used herein, the term "fabric" relates to a flexible material typically comprising a network of fibers produced by, for example and without limitation, weaving, knitting, crotcheting, knotting, felting or bonding. Typically, but not exclusively, "gauze" relates to thin, typically loosely woven cloth used for dressings and swabs or to any material made of an open, mesh-like weave.

In some embodiments, the OC comprises or is in the form of one or more sheets. The term "sheet" means a material that is thin in comparison to its length and breadth. In some embodiments, the sheets form a substantially flat configuration. In some embodiments, the sheet has a non-planar configuration. In some embodiments, the sheets are configured in a compressed position. In some embodiments, the OC is not in the form of powder or a plurality of particles. In some embodiments, the OC is not milled. By the term "OC is not in the form of powder or a plurality of particles" it is meant that: less than 50%, less than 40%, less than 30%, less than 20%, less than 10%, or even essentially no OC in the disclosed matrix, by weight, is or comprises a powdered form and milled particles; or at least 50%, at least 60%, at least 70%, at least 80%, at least 90%, or even essentially all OC in the disclosed matrix, by weight, is or comprises a powdered form and milled particles.

In some embodiments, by "expandable" it is meant to refer to a structure being capable of reaching larger volume than its initial volume upon exposure, contact with, or immersion in an aqueous solution such as water. The term "expandable" may refer to one or more directions in which the matrix may expand, e.g., radially expandable. As used herein, the term "radially expandable" includes segments that can be converted from a small configuration to a radially expanded, typically in cylindrical configuration. The term "expandable" may further refer to horizontally expandable (i.e. the width is increased), or vertically expandable (i.e. the height is increased). "Small configuration" may refer to at least one dimension, e.g., a diameter.

Additionally or alternatively, the term "expandable" may further refer to being either or both horizontally expandable and vertically expandable. Additionally or alternatively, the term "expandable" may further refer to being horizontally expandable, vertically expandable and/or radially expandable.

In some embodiments, the composition is expandable to at least 2, at least 3, at least 4, at least 5, at least 6, or at least 7 times, its original volume upon contact with an aqueous solution. In some embodiments, the composition is expandable to about 2, about 3, about 4, about 5, about 6, or about 7 times, its original volume, upon contact with an aqueous solution, including any value and range therebetween. In some embodiments, the composition is expandable to 2 to 5, 3 to 6, or 4 to 7, its original volume, including any value and range therebetween.

In some embodiments, the matrix is expandable to at least 2, at least 3, at least 4, at least 5, at least 6, or at least 7 times, its original volume within 2 to 6 sec, or 3 to 5, e.g., 4 sec upon contact with an aqueous solution at around room temperature.

In some embodiments, the matrix is expandable to 3 to 40, or 10 to 40 times its original volume within 2 to 6 sec, or 3 to 5, e.g., 4 sec upon contact with an aqueous solution at around room temperature. In some embodiments, the matrix is expandable to 15 to 30 times, its original volume within 2 to 6 sec, or 3 to 5, e.g., 4 sec upon contact with an aqueous solution at around room temperature.

In some embodiments, the matrix is expandable to 3, 4, 5, 6, 7, 8, 9, 10, 11, 12, 13, 14, 15, 16, 17, 18, 19, 20, 21, 22, 23, 24, 25, 26, 27, 28, 29, or 30 times, its original volume, including any value and range therebetween, within 2 to 6 sec, or 3 to 5, e.g., 4 sec upon contact with an aqueous solution at around room temperature.

Reference is made to the results presented in Table 2B, which are further illustrated in FIG. 4A to 6, demonstrating that an ORC density of about 0.95 to 1.2 gr/cm$^3$ provides optimal expansion after 4 sec, with the "FIBRILLAR" and "SNoW" exhibiting the highest expansion factor.

In some embodiments, the matrix comprises non-woven OC, expandable to at least 5 times its original volume within 4 sec upon contact with an aqueous solution at around room temperature.

In some embodiments, the matrix comprises OC, has a density of about 0.9 to about 1.25 gr/cm$^3$ and is expandable to at least 5 times its original volume within 4 sec upon contact with an aqueous solution at around room temperature. In some embodiments, the matrix comprises OC, has a density of 0.9 to about 1.25 gr/cm$^3$ and is expandable to about 5 to about 6 its original volume within 4 sec upon contact with an aqueous solution at around room temperature.

In some embodiments, the matrix comprises non-woven OC, has a density of about 0.9 to about 1.25 gr/cm³ and is expandable to at least 5 times its original volume within 4 sec upon contact with an aqueous solution at around room temperature. In some embodiments, the matrix comprises non-woven OC, has a density of about 0.9 to about 1.25 gr/cm³ and is expandable to about 5 to about 6 its original volume within 4 sec upon contact with an aqueous solution at around room temperature.

In some embodiments, the matrix comprises OC, has a density of about 1 to about 1.25 gr/cm³ and is expandable to at least 6 times its original volume within 4 sec upon contact with an aqueous solution at around room temperature. In some embodiments, the matrix comprises non-woven OC, has a density of about 0.9 to about 1.25 gr/cm³ and is expandable to about 6 to about 8 its original volume within 4 sec upon contact with an aqueous solution at around room temperature.

In some embodiments, the matrix comprises non-woven OC, has a density of about 1 to about 1.25 gr/cm³ and is expandable to at least 6 times its original volume within 4 sec upon contact with an aqueous solution at around room temperature. In some embodiments, the matrix comprises non-woven OC, has a density of about 0.9 to about 1.25 gr/cm³ and is expandable to about 6 to about 8 its original volume within 4 sec upon contact with an aqueous solution at around room temperature.

In some embodiments, the matrix comprises non-woven OC, has a density of about 0.9 to about 1.25 gr/cm³ and is expandable to at least 5 times its original volume within 4 sec upon contact with an aqueous solution at around room temperature. In some embodiments, the matrix comprises non-woven OC, has a density of about 0.9 to about 1.25 gr/cm³ and is expandable to about 5 to about 6 its original volume within 4 sec upon contact with an aqueous solution at around room temperature.

In some embodiments, the matrix comprises OC, has a density of about 1 to about 1.25 gr/cm³ and is expandable to at least 4 times its original volume within 4 sec upon contact with an aqueous solution at around room temperature. In some embodiments, the matrix comprises woven OC, has a density of about 1 to about 1.25 gr/cm³ and is expandable to at least 4 times its original volume within 4 sec upon contact with an aqueous solution at around room temperature. In some embodiments, the matrix comprises woven OC, has a density of about 0.9 to about 1.25 gr/cm³ and is expandable to about 4 to about 5 its original volume within 4 sec upon contact with an aqueous solution at around room temperature.

By "around the room temperature" it is meant to refer to at least one temperature value within the range of 10 to 40° C., or e.g., 15 to 37° C., e.g., 10, 15, 20, 25, 30, 35, 37, or 40° C., including any value and range therebetween.

In some embodiments, the matrix is capable of expanding to at least 70%, at least 80%, or at least 90% of its maximum expansion capacity within 20 to 40 seconds following immersion in an aqueous solution. In some embodiments, the matrix is capable of expanding to at least 70%, at least 80%, or at least 90% of its maximum expansion capacity within 20 to 40 seconds following immersion in an aqueous solution. In some embodiments, the matrix is capable of expanding to at least 70% of its maximum expansion capacity within 20 to 40 seconds following immersion in an aqueous solution. In some embodiments, the matrix is capable of expanding to at least 80% of its maximum expansion capacity within 20 to 40 seconds following immersion in an aqueous solution. In some embodiments, the matrix is capable of expanding to at least 90% of its maximum expansion capacity within 20 to 40 seconds following immersion in an aqueous solution. In some embodiments, the matrix is capable of expanding to 70 to 95% of its maximum expansion capacity within 20 to 40 seconds following immersion in an aqueous solution.

In some embodiments, the matrix is capable of expanding to at least 70%, at least 80%, or at least 90% of its maximum expansion capacity within about 30 seconds following immersion in an aqueous solution. In some embodiments, the matrix is capable of expanding to at least 70% of its maximum expansion capacity within about 30 seconds following immersion in an aqueous solution. In some embodiments, the matrix is capable of expanding to at least 80% of its maximum expansion capacity within about 30 seconds following immersion in an aqueous solution. In some embodiments, the matrix is capable of expanding to at least 90% of its maximum expansion capacity within about 30 seconds following immersion in an aqueous solution. In some embodiments, the matrix is capable of expanding to 70 to 95% of its maximum expansion capacity within about 30 seconds following immersion in an aqueous solution.

The term "expansion" means an increase in the volume. The terms "expansion capacity", "maximum expansion" or "maximum expansion capacity", which may be used interchangeably, mean the maximal volume the matrix can reach following contact with aqueous media.

In some embodiments, the matrix has a pre-expansion volume ranging from about 0.4 to about 1.5 cm³, or from about 0.4 to about 1.5 cm³. In some embodiments, the matrix has a pre-expansion volume ranging from about 0.5 to about 0.75 cm³. In some embodiments, the matrix has a pre-expansion volume of about 0.4, about 0.5, about 0.6, about 0.7, or about 0.8 cm³, including any value and range therebetween.

Accordingly, in some embodiments, the matrix has a pre-expansion total surface area ranging from total about 3 to about 5 cm². In some embodiments, the matrix has a pre-expansion total surface area ranging from total about 3 to about 5 cm². In some embodiments, the matrix has a pre-expansion total surface area ranging from total about 3.5 to about 4.5 cm². In some embodiments, the matrix has a pre-expansion total surface area of about 3 cm², about 3.1 cm², 3.2 cm², about 3.3 cm², about 3.4 cm², about 3.5 cm², 3.6 cm², about 3.7 cm², 3.8 cm², about 3.9 cm², about 4 cm², about 4.1 cm², 4.2 cm², about 4.3 cm², 4.4 cm², about 4.5 cm², about 4.6 cm², about 4.7 cm², 4.8 cm², about 4.9 cm², or about 5 cm², including any value and range therebetween.

The term "matrix" is used herein interchangeably with the terms "composition" and "composition-of-matter", and defines a 3-dimensional structure that is formed from e.g., the OC-material. The matrices described herein may differ in their secondary, tertiary and quaternary structures from the OC used in their formation.

The term "biodegradable" as used in the context of the present disclosure describes a material which can decompose under physiological and/or environmental conditions into breakdown products. Such physiological and/or environmental conditions include, for example, hydrolysis (decomposition via hydrolytic cleavage), enzymatic catalysis (enzymatic degradation), and mechanical interactions. This term typically refers to substances that decompose under these conditions such that at least 30 weight percent of the substance decompose within a time period shorter than one year. The term "biodegradable" as used in the context of the present disclosure also encompasses the term "bioresorbable", which describes a substance that decomposes under physiological conditions to break down to products that undergo bioresorption into the host-organism, namely, become metabolites of the biochemical systems of the host-organism.

The matrix may be in any shape or form, e.g., having a substantially, polygonal or rectangular (including substantially square), substantially circular and/or substantially oval cross-section along at least one axis. For example, the matrix may have a substantially box-like shape, having a substantially rectangular cross-section (optionally with rounded corners) along 3 axes; a substantially cylindrical shape, having substantially circular and/or substantially oval cross-section along one axis, and a substantially rectangular cross-section (optionally with rounded corners) along 2 axes; or a substantially spherical or ovoid shape, having a substantially circular and/or substantially oval cross-section along 3 axes. Other shapes, forms and sizes of the disclosed composition may be selected from, without being limited thereto, plugs, disks, rods, tubes, conical cylinders, spheres, half and spheres, cubes, rectangles, triangles, or saucers.

As used herein, the terms "contact", or "exposure" in the context of aqueous solution refer to any manner in which a composition of the present disclosure is brought into a position where it can at least partially absorb the aqueous solution. The term "aqueous solution" refers to a solution in which water is the dissolving medium or solvent. In some embodiments, the aqueous solution comprises body fluid such as blood. For example, "contacting" may comprise immersing the composition in a bleeding site.

Figure 1A:
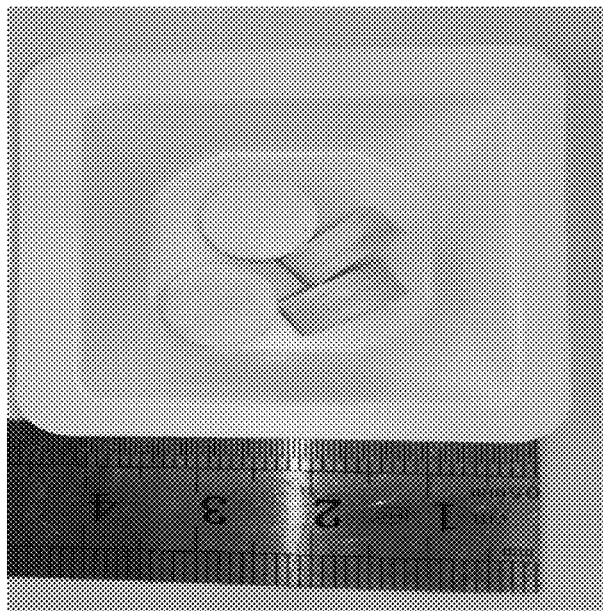

In some embodiments, the composition is in the form of pellet or tablet, (e.g., optionally as shown in FIGS. 1A-B). In some embodiments, the composition is in the form of a wound dressing. The term "wound dressing", as used in the context of the present disclosure, refers to dressings for topical application onto/into wound and/or bleeding site. Terms such as "wound plaster", "wound bandage" or "wound covering" can also be used synonymously.

In some embodiments, the matrix has a density of 0.7 to 1.4 $gr/cm^3$, 0.7 to 1.3 $gr/cm^3$, 0.8 to 1.2 $gr/cm^3$, 0.9 to 1.2 $gr/cm^3$, 1.1 to 1.2 $gr/cm^3$, 0.8 to 1.3 $gr/cm^3$, 0.7 to 1.1 $gr/cm^3$, 0.7 to 1 $gr/cm^3$, 0.7 to 0.9 $gr/cm^3$, 0.7 to 0.8 $gr/cm^3$. In some embodiments, the matrix has a density of 0.7, 0.8, 0.9, 1, 1.1, 1.2, 1.3, or 1.4 $gr/cm^3$, including any value and range therebetween. In some embodiments, the matrix has a density of about 1.2 $gr/cm^3$. Herein, by "density", it is meant to refer to the non-expanded state, i.e. prior to exposure to aqueous solution.

In some embodiments, the volume of the matrix may be greater than 1 $mm^3$. In some embodiments, the volume of the matrix may be at least 5 $mm^3$. In some embodiments, the volume of the matrix may be greater than 10 $mm^3$. In some embodiments, the volume of the matrix may be about 5, 10, 15, 20, 25, 30, 35, 40, 45, 50, 55, 60, 65, 70, 75, 80, 85, 90, 95, or 100 $mm^3$, including any value and range therebetween. In some embodiments, the volume of the matrix may be greater than 100 $mm^3$. In some embodiments, the volume of the matrix may be about 1 to 100, 1 to 10, e.g., about 5 $mm^3$. Herein, by "volume of the matrix", it is meant to refer to the non-expanded state, i.e. prior to exposure to aqueous solution.

The term "oxidized cellulose" (or "OC") refers to a cellulose derivative in which at least some of the primary alcohol groups, e.g., on the carbon 6 of the anhydroglucose unit is oxidized to a carboxylic acid, and is optionally functionalized. OC may include materials, products, articles, or compositions comprising or consisting essentially of OC, e.g., a dressing, fibrin glue, synthetic glue, pad, matrix, powder, tab, pill, suture, fiber, stent, implant, scaffold, solution, gel, wax, gelatin and the like.

OC may be produced by applying an oxidizing agent on cellulose. The oxidizing agent may be selected from, without being limited thereto, chlorine, hydrogen peroxide, peracetic acid, chlorine dioxide, nitrogen dioxide, persulfates, permanganate, dichromate-sulfuric acid, hypochlorous acid, hypohalites, periodates, or any combination thereof, and/or a variety of metal catalysts. Oxidized cellulose may contain carboxylic acid, aldehyde, and/or ketone groups, instead of, or in addition to the original hydroxyl groups of the starting material, cellulose, depending on the nature of the oxidant and reaction conditions.

The OC in the compositions of the invention is typically, but not exclusively, in the form of pellet, capsule, or tablet.

The term "tablet" is used in its common context, and refers to a solid composition made by compressing and/or molding a mixture of compositions in a form convenient for application to any body cavity. This term includes matrix e.g., pharmaceutical compositions of all shapes and sizes. The term "pellet" shall herewith include granules and tablets which can be understood as pellets of various sizes and shapes.

In exemplary embodiments, OC has been oxidized to contain carboxyl moieties in amounts effective to provide biodegradability. For example, U.S. Pat. No. 3,364,200 discloses the preparation of carboxylic-oxidized cellulose with an oxidizing agent such as dinitrogen tetroxide in a Freon medium. U.S. Pat. No. 5,180,398 discloses the preparation of carboxylic-oxidized cellulose with an oxidizing agent such as nitrogen dioxide in a per-fluorocarbon solvent. After oxidation by either method, the fabric may be thoroughly washed with a solvent such as carbon tetrachloride, followed by aqueous solution of 50 percent isopropyl alcohol (IPA), and finally with 99% IPA. Prior to oxidation, the fabric can be constructed in the desired woven or nonwoven construct.

Typically, hemostats that are compatible with acid-sensitive species comprise e.g., fabric substrates prepared from a biocompatible, aldehyde-oxidized polysaccharide. In such exemplary hemostats, the polysaccharide contains an amount of aldehyde moieties effective to render the modified polysaccharide biodegradable, meaning that the polysaccharide is degradable by the body into components that are either resorbable by the body, or that can be passed readily by the body. More particularly, the biodegraded components do not elicit permanent chronic foreign body reaction when they are absorbed by the body, such that substantially no permanent trace or residual of the component is retained at the implantation site.

In certain embodiments of the present disclosure, the OC comprises layers prepared from biocompatible, biodegradable, aldehyde-oxidized regenerated cellulose. In some embodiments, the OC comprises or consists essentially of oxidized regenerated cellulose (ORC) e.g., aldehyde-oxidized regenerated cellulose. In some embodiments, the aldehyde-oxidized regenerated cellulose is one comprising repeating units of Structure II in U.S. Pat. No. 8,709,463. In some embodiments, ORC is used to prepare hemostats. Typically, regenerated cellulose is preferred due to its higher degree of uniformity versus cellulose that has not been regenerated. Exemplary regenerated cellulose and a detailed description of how to make ORC is set forth in U.S. Pat. Nos. 3,364,200 and 5,180,398.

As indicated above, in some embodiments, the degree of oxidation of the OC may be important to its functional properties such as biocompatibility and bioabsorbability. Products including various degrees of OC oxidation exist, such as a surgical hemostat in which carboxylic acid groups are present at a concentration of 18 to 21% by weight of the oxidized cellulose.

As used herein with reference to OC, the terms "oxidation level", "degree of oxidation", "carboxyl content", and "carboxylation level" are interchangeable, and may be determined per United States Pharmacopeia (USP) 23-NF18.

Accordingly, in some embodiments, the carboxyl content of the OC is 12 to 24%, by weight. In some embodiments, the carboxyl content of the OC is 12 to 23%, by weight. In some embodiments, the carboxyl content of the OC is 12 to 22%, by weight. In some embodiments, the carboxyl content of the OC is 12 to 21%, by weight.

In some embodiments, the carboxyl content of the OC is 16 to 24%, by weight and the composition can function as a hemostat. In some embodiments, the carboxyl content of the OC is 17 to 23%, by weight. In some embodiments, the carboxyl content of the OC is 18 to 22%, by weight. In some embodiments, the carboxyl content of the OC is 18 to 21%, by weight.

In some embodiments, the carboxyl content of the OC is 12 to 18%, by weight. In some embodiments, the carboxyl content of the OC is 12 to 17%, by weight. In some embodiments, the carboxyl content of the OC is 12 to 16%, by weight.

In some embodiments, the carboxyl content of the OC is 12%, 13%, 14%, 15%, 16%, 17%, 18%, 19%, 20%, 21%, 22%, 23%, or 24%, by weight, including any value and range therebetween.

It is appreciated that while the usual source for OC is plant material, OC may also be derived from a bacterial source. In some embodiments, the OC is derived from a plant source.

In some embodiments, the cellulose for use with the present invention does not include CMC.

According to some embodiments, the matrix comprises fibers prepared from a biocompatible polymer(s) and comprises a surface that possesses properties suitable for use as a hemostat, e.g., strength, flexibility and porosity.

In certain embodiments of the invention, the OC (e.g., ORC) may be further combined with a hemostatic agent, or other biological or therapeutic compounds, moieties or species, including drugs and pharmaceutical agents. In some embodiments, to improve the hemostatic performance, scaffolds based on the above materials can be combined with biologically-derived clotting factors, such as thrombin and fibrinogen. In yet another embodiment, the disclosed ORC-based composition may be combined with an additive, such as carboxymethyl cellulose (CMC), calcium salt, anti-infective agent, hemostasis promoting agent, gelatin, collagen, saline, or any combination thereof.

In further embodiments of the present invention, the disclosed ORC-based composition may be combined with various additives to further improve the hemostatic properties, wound healing properties, and handling properties. Utilizing additives known to those skilled in the art includes for example: hemostatic additives such as gelatin, collagen, cellulose, chitosan, polysaccharides, starch; biologics-based hemostatic agents as exemplified by thrombin, fibrinogen, and fibrin. Additional biologics hemostatic agents include, without limitation, procoagulant enzymes, proteins, and peptides. Each such agent can be naturally occurring, recombinant, or synthetic, and may be further selected from: fibronectin, heparinase, Factor X/Xa, Factor VII/VIIa, Factor IX/IXa, Factor XI/XIa, Factor XII/XIIa, tissue factor, batroxobin, ancrod, ecarin, von Willebrand Factor, albumin, platelet surface glycoproteins, vasopressin and vasopressin analogs, epinephrine, selectin, procoagulant venom, plasminogen activator inhibitor, platelet activating agents, synthetic peptides having hemostatic activity, derivatives of the above, and any combination thereof anti-infective agents, such as chlorhexidine gluconate (CHG), triclosan, silver, and similar anti-bacterial/microbial agents that are known in the art; additives that increase the stickiness of the hemostat; and other additives known in the art.

In some embodiments, the OC, such as ORC, is provided in the form of a pellet (compressed or non-compressed), a bead, a granule, an aggregate, a fiber(s), sheets (including a woven, nonwoven, knitted, milled or fine fiber and combinations thereof), all either independently used or dispersed in a pharmaceutically acceptable vehicle or in other forms.

Non-limiting examples for OC-based material that are either in pellet form, or may be ground to first obtain a plurality of sheets and may be utilized, include different textured OC or ORC material, for example, and without being limited thereto, INTERCEED® absorbable adhesion barrier, SURGICEL® Original absorbable hemostat (loose knit of ORC), SURGICEL® NU-KNIT® absorbable hemostat (densely woven knit of ORC), SURGICEL® FIBRILLAR™ absorbable hemostat (soft, lightweight, layered ORC), SURGICEL® SNoW™ absorbable hemostat (structured non-woven fabric, needle punched with interlocking fibers) and SURGICEL® Powder absorbable hemostat, or GelitaCel® resorbable cellulose surgical dressing from Gelita Medical BV, Amsterdam, The Netherlands.

SURGICEL® Powder absorbable hemostat is a powder that comprises aggregate of small ORC fiber fragments that may spread across a large surface area and form a durable clot that will not be washed away or rebleed when irrigated.

Typically, woven fabric is composed of two sets of yarns. One set of yarns, the warp, runs along the length of the fabric. The other set of yarns, the fill or weft, is perpendicular to the warp. Woven fabrics are held together by weaving the warp and the fill yarns over and under each other.

"Non-woven fabric" refers to a fabric-like material made from long fibers, bonded together by chemical, mechanical, heat or solvent treatment. The term is used in the textile manufacturing industry to denote fabrics, such as felt, which are neither woven nor knitted. Thus, the phrase "non-woven" refers to a sheet, web or mat of directionally or randomly oriented fibers, where fibers are not intercalated but rather bonded through various means, including e.g., friction, cohesion and/or adhesion. The term "non-woven fabric" also includes, but is not limited to, bonded fabrics, formed fabrics, or engineered fabrics, that are manufactured by processes other than spinning, weaving or knitting.

Typically, but not exclusively, the term "non-woven fabric" also relates to a porous, textile-like material, composed primarily or entirely of staple fibers assembled in a web, sheet or batt, usually in flat sheet form. The structure of the non-woven fabric is based on the arrangement of, for example, staple fibers that are typically arranged more or less randomly. The tensile, stress-strain and tactile properties of the non-woven fabric ordinarily stem from fiber to fiber friction created by entanglement and reinforcement of, for example, staple fibers, and/or from adhesive, chemical or physical bonding. Notwithstanding, the raw materials used to manufacture the non-woven fabric may be yarns, scrims, netting, or filaments made by processes that include spinning, weaving or knitting (as described e.g., in Patent Application having the Publication number: EP1802358A2).

Typically, knitted fabrics are made from only one set of yarns, all running in the same direction. Some knits have their yarns running along the length of the fabric, while others have their yarns running across the width of the fabric. Knit fabrics may be held together by looping the yarns around each other. Knitting creates ridges in the resulting fabric.

As shown in the Examples section below, the ORC originated from short fibers ("ORC Short") expanded up to approximately 5 times its original volume, while ORC made of long fibers ORC ("ORC Long") expanded up to 3 times its original volume. Increasing the compression pressure to 2 or 5 tons did not have a beneficial effect on the expansion factor. The non-woven fabrics exhibited a superior overall expansion effect. Typical size distribution of ORC fiber types, "ORC Long" or "ORC Short" is as described in the Examples section below (Table 1).

In some embodiments, the above-mentioned forms (e.g., non-woven, knitted, etc.) of the OC-based materials, does not necessarily remain the same in the compressed form of the disclosed matrix.

The fabricated compressed ORC materials A, B, C and D (as described in the Examples section below) all exhibited superior expansion factors to the milled powders.

The compositions of the invention are non-aqueous compositions, which means that the main liquid in the compositions is not water and the compositions have very low water content or no water at all prior to their immersion in an aqueous environment. Thus, in some embodiments, the water content of the composition is lower than 10% (w/w). In some embodiments, the water content of the composition is lower than 8% (w/w). In some embodiments, the total water content of the composition is lower than 5%, 4%, 3%, 2%, or 1% (w/w). In some embodiments, the composition does not contain water. In some embodiments, the composition does not comprise any solvent.

In some embodiments, the matrix further comprises a pharmaceutically acceptable excipient or additive. Excipients and additives may include any pharmaceutically suitable excipient, such as, without being limited thereto, calcium salt, human albumin, mannitol, sodium acetate, sodium chloride, sodium citrate dihydrate, gluconate buffer, saccharose, glycine, sodium acetate, histidine, and polyethylene glycol (PEG).

Calcium salt used with the invention may be in the form of calcium chloride salt. Alternatively, additional salts may be used, such as calcium acetate and/or calcium citrate.

In some embodiments, the composition may further comprise a biologically active agent. Non-limiting biologically active agents that may be included in the composition include therapeutic agents such as antibiotics, anti-inflammatory agents, growth factors, or clotting factors as described above. For example, the composition may further comprise fibrinogen or thrombin.

As used herein, "thrombin" denotes an activated enzyme which results from the proteolytic cleavage of prothrombin (factor II). Thrombin may be produced by a variety of methods of production known in the art, and includes, but is not limited to, recombinant thrombin and plasma derived thrombin.

Human thrombin is a 295 amino acid protein composed of two polypeptide chains joined by a disulfide bond. Both human and non-human (e.g., bovine) thrombin may be used within the scope of the present disclosure.

The term "fibrinogen" without more is intended to include any type of fibrinogen such as, without limitation fibrinogen in a cryoprecipitate. Fibrinogen, therefore, refers to monomeric and dimeric fibrinogen molecules having the monomer structure (AαBβγ), hybrid molecules, and variants thereof, whether naturally occurring, modified, or synthetic. The term "fibrinogen" refers generally to fibrinogen from humans, but may include fibrinogen of any species, especially mammalian species.

Any preparation for therapeutic use must be sterile. Especially when handling blood products, the sterility issue is crucial, and specifically the issue of viral inactivation. In general, viral inactivation may be carried out by any method, including solvent detergent, heat inactivation, irradiation, and nanofiltration. Typically, the standard for viral inactivation requires using two different methods. Additionally, the U.S. Food and Drug Administration (FDA) standard for sterility requires filtration.

In another embodiment, the disclosed composition may be used in conjunction with a backing, pad, scaffold, or matrix to provide mechanical strength to cover the wound surface. In this case, the instant matrix is supported on a pad for ease of application or tamponade.

In some embodiments, the matrix is characterized by an antimicrobial effectiveness. In some embodiments, the matrix is for antimicrobial use e.g., in inhibiting or reducing the formation of load of a microorganism. As used herein, the term "antimicrobial" is intended to include destroying or inhibiting the growth of microorganisms such as pathogenic bacteria. The antibacterial effectiveness, and in some embodiments, may be for use in inhibiting or reducing the formation of load of a microorganism.

It is appreciated that the composition may be applied, for example, by sticking the composition directly onto the bleeding site. Accordingly, the composition does not need to be further spread on or applied to a solid surface, object, or other solid medium such as a strip or a film in order to be in the appropriate form for applying to the bleeding site. Nevertheless, a suitable applicator may be used in order to apply, locate, spread or stick the composition onto the bleeding site, for the purpose of easy access and handling.

As provided herein, the OC matrix may be used as an immediate hemostat without the need for time consuming and cumbersome manual compression at the wound site. Through the compression exerted by expansion of the material itself in the wound site, following absorption with blood, the compressed material can stop or reduce the bleeding without further external compression.

In an aspect of the present invention, there is provided a method of treating a wound comprising the step of applying (e.g., contacting) the disclosed biodegradable hemostatic matrix in any embodiment thereof onto and/or into the wound of a subject in a need thereof.

By "treating a wound" it further meant to encompass reducing blood loss at a bleeding site of a tissue, e.g., in a patient undergoing surgery. Accordingly, in some embodiments, the method is for reducing blood loss at a bleeding site of a tissue, e.g., in a patient undergoing surgery, comprises contacting the disclosed composition in an embodiment thereof with the bleeding site.

Figure 2:
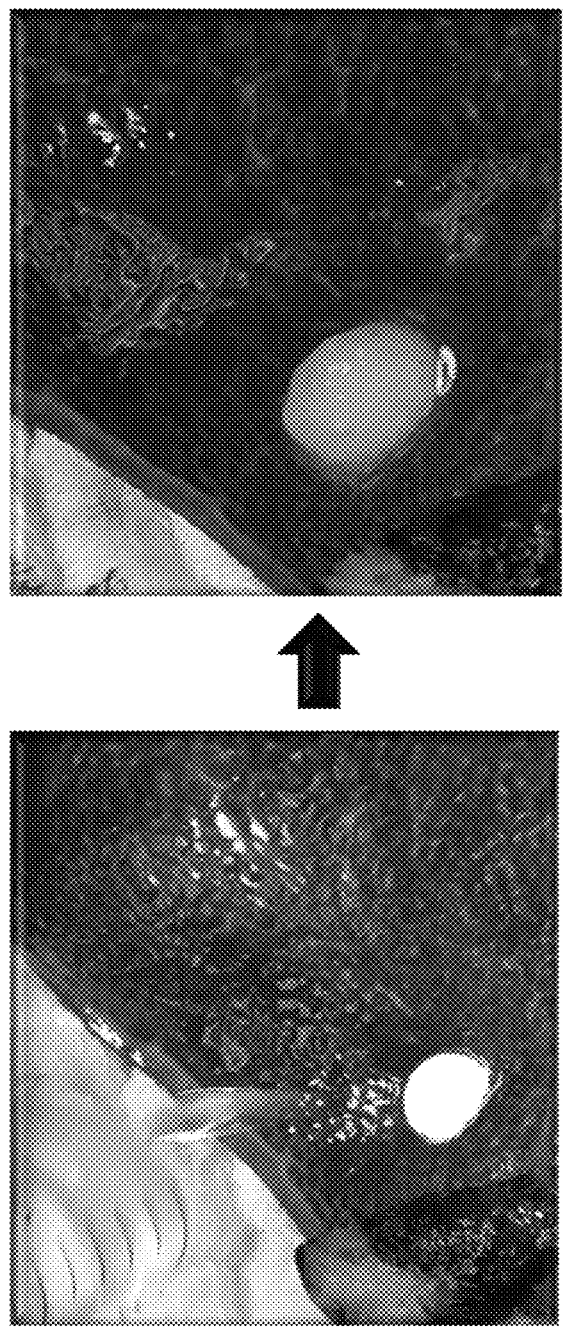
FIG. 2 presents photographs demonstrating the application of the disclosed matrix in the form of a pellet during a surgical procedure: the white pellet is inserted to a bleeding site (left panel) and thereafter absorbs blood and expands rapidly to from its original volume to facilitate efficient hemostasis (right panel, following the arrow).

Reference is now made to FIG. 2, demonstrating the ability of the composition of the invention to expand upon exposing to body fluid, while taking on the shape of the wound site.

As used herein, the term "subject" shall mean any animal including, without limitation, a human, a mouse, a rat, a rabbit, a non-human primate, or any other mammal. In some embodiments, the subject is human, e.g., a human patient. The subject may be male or female.

Accordingly, the disclosed matrix in any embodiment thereof, is for use in controlling bleeding in a soft tissue of a subject in a need thereof. The term "soft tissues" as used herein relates to body tissue that is not hardened or calcified. This term especially relates to soft tissues that are vascularized and therefore may be a source of bleeding. Examples for such tissues include but are not limited to connective tissue (such as tendons, ligaments, fascia, skin, fibrous tissues, fat, and synovial membranes), muscles, and internal organs. In general, soft tissues are meant to exclude bone tissue.

In some embodiments, the composition is homogeneous. As used herein, by "homogeneous" it is meant to refer to a uniform composition and texture throughout, i.e. having a density that varies within less than ±20%, less than ±15%, less than ±10%, less than ±5%, less than ±2%, or less than ±1%.

A desired combination of properties of the disclosed matrix, e.g., having a density ranging from 0.8 to 1.2 gr/cm$^3$, and being expandable to at least 3 times its original volume within 4 sec upon contact with an aqueous solution, was found to be achievable e.g., by compressing the OC material e.g., non-woven material ORC source.

Accordingly, there is provided a method of making the disclosed hemostatic matrix according to any embodiment thereof, the method comprising the step of compressing or compacting an OC-based material by applying on a surface thereof a pressure ranging from about 0.2 to about 7 ton/per cm$^2$. In some embodiments, the method comprises the step of compressing or compacting an OC-based material by applying on one or more surfaces thereof a pressure ranging from 0.3 to 3.5 ton/per cm$^2$. In some embodiments, the method comprises the step of compressing or compacting an OC-based material by applying on a surface thereof a pressure of 0.2, 0.3, 0.4, 0.5, 0.5, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, or 7 ton/per cm$^2$, including any value and range therebetween.

In another aspect of the present disclosure, there is provided a matrix produced by the method of compressing an OC-based material by applying on a surface thereof a pressure indicated herein. In some embodiments, the compression is applied by applying a pressure e.g., using a hydraulic press. In some embodiments, the pressure applied ranges from about 0.2 to about 7 ton/per cm$^2$, 0.3 to 3 ton, or 0.5 to 2 ton per 1 cm$^2$, e.g., 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 3, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, or 7 ton per 1 cm$^2$, including any value and range therebetween.

In some embodiments of the method, the OC material comprises ORC. In some embodiments of this method, the ORC is in the non-woven form. In some embodiments, the method further comprises the step of mixing the OC material with one or more additives selected from, without being limited thereto, calcium salt, anti-infective agent, and hemostasis promoting agent.

As used herein the term "about" refers to ±10%.

The terms "comprises", "comprising", "includes", "including", "contains", "containing", "has", "having", and their conjugates mean "including but not limited to". The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an", and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, and unless stated otherwise, the terms "by weight", "w/w", "weight percent", or "wt. %", which are used herein interchangeably describe the concentration of a particular substance out of the total weight of the corresponding mixture, solution, formulation or composition.

As used herein, the term "bleeding" refers to extravasation of blood from any component of the circulatory system.

A "bleeding" thus encompasses unwanted, uncontrolled and often excessive bleeding in connection with surgery, trauma, or other forms of tissue damage, as well as unwanted bleedings in patients having bleeding disorders.

As used herein, the terms "controlling" "preventing" or "reducing", which may be used herein interchangeably in the context of the bleeding, including any grammatical inflection thereof, indicate that the rate of the blood extravagated is essentially nullified or is reduced by at least 10%, at least 20%, at least 30%, at least 40%, at least 50%, at least 60%, at least 70%, at least 80%, at least 90%, or even by 100%, of the initial rate of bleeding, compared to situation lacking the contact of the disclosed composition in/on the bleeding site. Methods for determining a level of appearance of bleeding are known in the art.

Further, in some embodiments, the terms "controlling", "preventing", or "reducing", in the context of the bleeding are also meant to encompass at least partially sealing blood vessels at the bleeding site either in soft tissues.

In those instances where a convention analogous to "at least one of A, B, and C, etc." is used, in general such a construction is intended in the sense one having skill in the art would understand the convention (e.g., "a composition having at least one of A, B, and C" would include but not be limited to compositions that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A", "B", or "A and B".

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials and Methods

Materials

Table 1 below presents ORC form used for exemplary expansion experiments.

TABLE 1

| Material | Form* |
|---|---|
| ORC tablet A | Knitted fabric |
| ORC tablet B | Knitted fabric |
| ORC tablet C | Non-woven fabric |
| ORC tablet D | Non-woven fabric |
| "ORC short" | milled ORC powder containing particles with size distribution of D90 less than 177 μm and D50 less than 95 μm |
| "ORC Long" | milled ORC powder containing particles with size distribution of D90 less than 350 μm and D50 is less than 167 μm |

*Tablets "A" and "B" are made from a Knitted fabric (A = SURGICEL original; B = NU-KNIT); Tablets "C" and "D" are made from either a woven, or non-woven (non-knitted) material (C = FIBRILLAR; D = SNoW).

In additional exemplary procedures, the following ORC materials: SURGICEL, NU-KNIT, FIBRILLAR, SNoW, and Milled ORC were further tested as described below.

Sample Preparation

Samples of 0.5 g were weighed from each material. Weighed samples were pressed into a circular 1 cm diameter tablet mold. 0.5, 2, and 5 tons compression force was administered resulting in ORC tablets which varying in their compression levels.

Weighed samples were placed within a round pellet die mold having a 1 cm diameter. In exemplary procedures, the mold used was a metallic cylinder having a 1 cm diameter. A metallic rod having a similar diameter to the mold opening was inserted into the mold and placed on top of the sample material. Force was used on the rod in order to compress the sample while the rod continues to be inserted into the mold containing the sample. The force was applied by the rod is in the vertical axis of the cylindrical mold. The force was applied by a manual hydraulic press until reaching a predetermined force such as 0.5, 2, and 5 tons compression force. Once achieved, the rod was removed, and the resulting tablets were removed from the mold.

Methods

The thickness of each pressed sample was measured using calipers to calculate its initial volume. A clear graduated 12 mm diameter cylinder was filled up to 10 mL with saline. Next, the 10 mm diameter sample tablet was released into the saline in the graduated cylinder from the top face of the cylinder. At the point-of-release a timer was started. The samples, mostly constrained horizontally, began to absorb the liquid and expand predominantly in the vertical axis. The volume of the expending sample was visualized and evaluated when appropriate through the clear graduated cylinder. Expansion factor was evaluated at 4 seconds after point-of-release. The maximal expansion factor as well as the length of time until maximum expansion was achieved, were documented.

Instruments:
1. Caliper—Sylva 'SCal pro IP67'
2. Graduated 12 mm diameter cylinder—'Plasti Brand'
3. Manual Hydraulic Press—Specac Atlas series 15-ton press
4. 10 mm Evacuable Pellet Die—Specac
5. Digital Timer TM-44—MICROTEMP ELECTRICS CO., LTD Example 1: Degree of Expansion In exemplary procedures, the speed and degree of expansion of expandable tablets produced, inter alia, from different textured ORC material were assessed. The results provide an estimate as to the potential of each type of compressed ORC to function as an efficacious hemostat in various blood loss scenarios.

Expansion Factor: The degree of expansion (Expansion factor) is defined as the multiple of the original volume (mL) at maximum expansion. For example, if the original volume of a tablet was 2 cm$^3$, and the maximum expansion volume was 8 cm$^3$, the expansion factor would be 4.

Time to maximum expansion: The amount of time from the tablet's exposure to saline until their full expansion was measured. Time was measured up to 300 seconds.

Figure 3A:
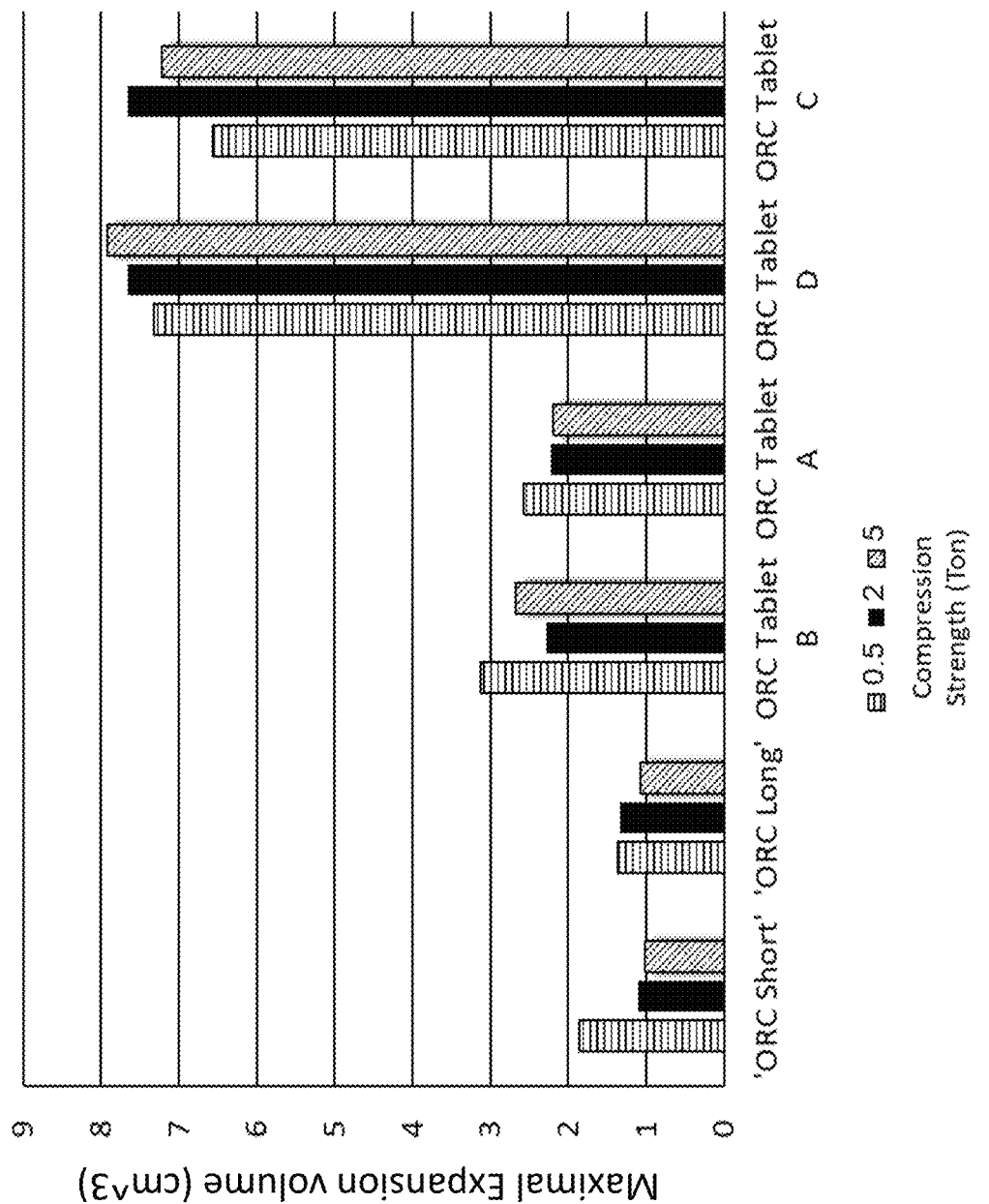
FIGS. 3A-3B present bar graphs showing the maximal expansion volume ($cm^3$) in saline of various oxidized regenerated cellulose (ORC) matrix samples as described in the Examples section (Table 2A), compressed under a 0.5, 2, and 5-ton compression strength (T) (FIG. 3A); and respective times (in sec) taken for each sample to reach maximal expansion (FIG. 3B). In each bar triplet, the left one refers to 0.5 Ton (T), the middle one refers to 1 T, and the right one refers to 5 T.
Figure 3B:
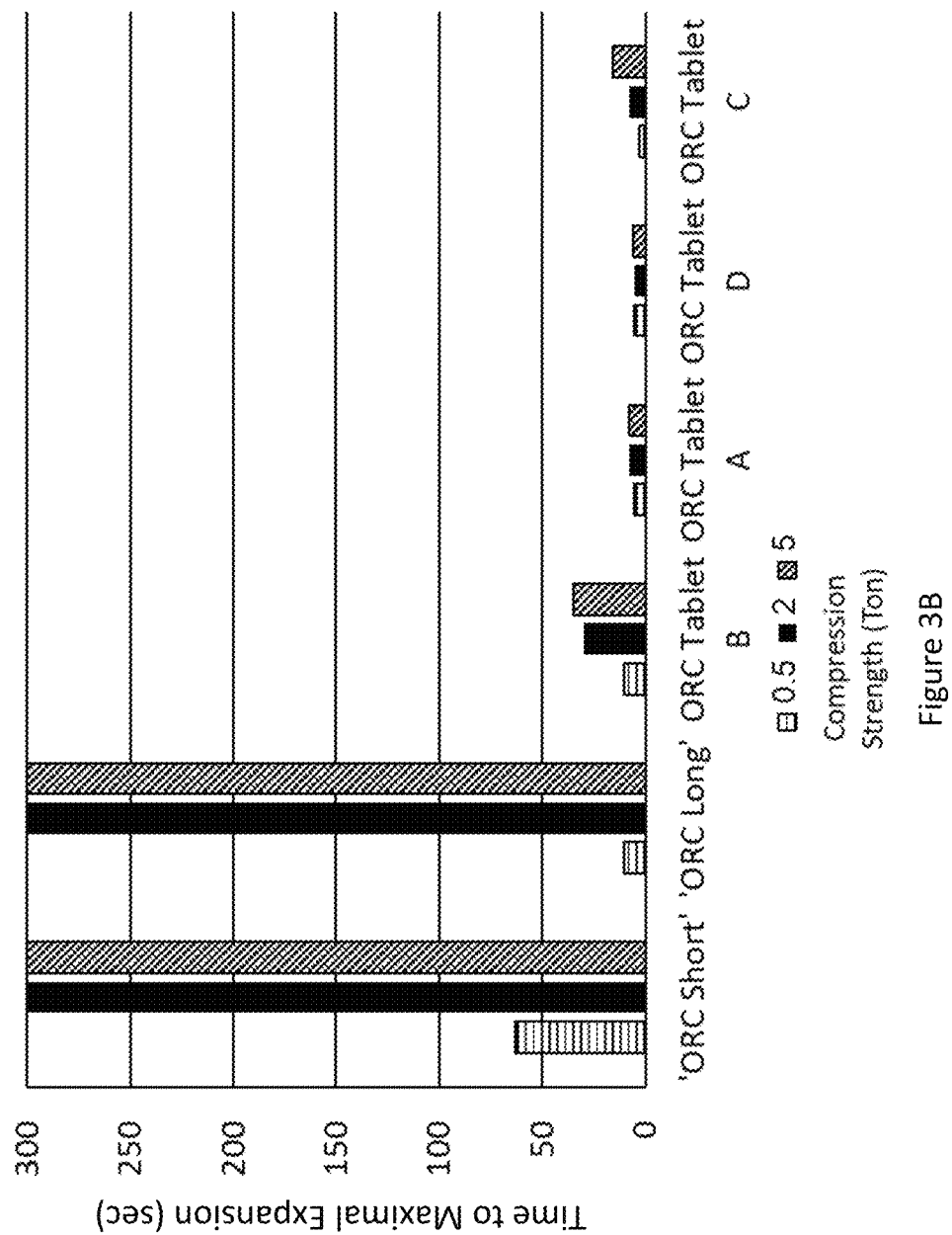

Results are summarized in Tables 2A and 2B showing the expansion factor and time to expansion of ORC tablets (fixed to 4 sec in Table 2B) exposed to saline, and are further illustrated in FIGS. 3A and 3B.

TABLE 2A

| Composition | Pressure (Ton per 0.785 cm$^2$) | Maximal* Expansion (mL) | Time to expansion (sec) |
|---|---|---|---|
| ORC Short tablet | 0.5 | 1.86 | 65 |
| | 2 | 1.10 | 300 |
| | 5 | 1.02 | 300 |
| ORC Long tablet | 0.5 | 1.36 | 10 |
| | 2 | 1.34 | 300 |
| | 5 | 1.08 | 300 |
| ORC tablet B | 0.5 | 3.12 | 10 |
| | 2 | 2.28 | 30 |
| | 5 | 2.68 | 35 |
| ORC tablet A | 0.5 | 2.58 | 5 |
| | 2 | 2.23 | 8 |
| | 5 | 2.19 | 8 |
| ORC tablet D | 0.5 | 7.32 | 5 |
| | 2 | 7.66 | 5 |
| | 5 | 7.92 | 6 |
| ORC tablet C | 0.5 | 6.57 | 3 |
| | 2 | 7.66 | 8 |
| | 5 | 7.22 | 16 |

*The initial volume was similar for all the samples

The samples of the milled ORC "ORC Short" and "ORC Long" exhibited the least expansion volume. Moreover, when exposed to saline the fibers dissolve to a certain extent and immediately begin to break down. When compressed under 0.5-ton (per 0.785 cm$^2$) pressure, the "ORC short" expanded up to approximately 5 times its original volume, while "ORC Long" expanded up to 3 times its original volume. Increasing the compression pressure to 2 or 5 tons did not have a beneficial effect on the expansion factor. However, increasing the compression strength hindered the tablets capability to expand resulting in time to max expansion that surpassed the 5-minute time limit defined for the assay.

The fabricated compressed material A, B, C and D all exhibited superior expansion factors to the milled powders.

Of the knitted fabrics (materials A and B)—material B exhibited slightly better expansion properties than material A, with no apparent effect of increased pressure on expansion degree. However, the time required for the maximum expansion was significantly shorter in material A, compared to material B in all compression strengths (5-8 sec; 10-35 sec). In both fabrics—like in the powdered ORC—a 0.5 ton compressed tablet expanded faster than the more compressed tablets.

A 0.5-ton compression reduced the expansion factor for both fabrics. Time to maximal expansion was very fast in the material D tablet (5 sec) for all the compression pressures. Material C tablets exhibited direct effect of compression on "time to max expansion" in which increased tablet pressure directly increased the time to expansion from 3 sec (0.5 ton) to 16 sec (5 tons). Materials A and C reached their maximal expansion at the same time (8 sec at 2-ton compression) (see FIG. 3B). The 2-ton compression was chosen given its combined results in expansion volume and time of expansion (as shown FIGS. 3A and 3B).

Figure 4A:
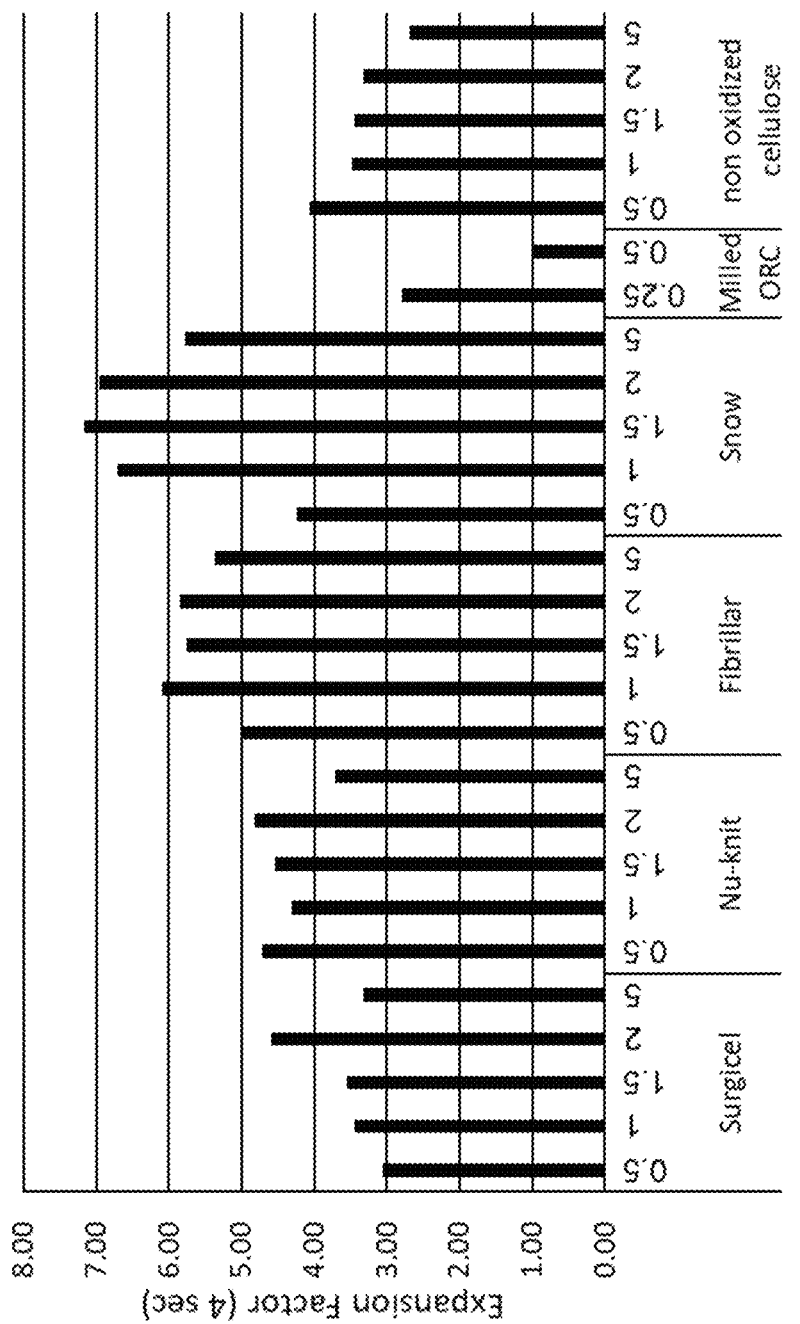
FIGS. 4A-4C present bar graphs based on data presented in Table 2B showing the expansion volume in saline of various ORC matrix samples and for the Gauze pad (non-oxidized cellulose) compressed under different forces ranging from 0.25 to 5 ton (compression strength; T) as: expansion factor after 4 sec (FIG. 4A); maximal expansion factor (FIG. 4B); and combined bars of maximal expansion factor and expansion factor after 4 sec for the tested ORC materials (FIG. 4C).
Figure 4B:
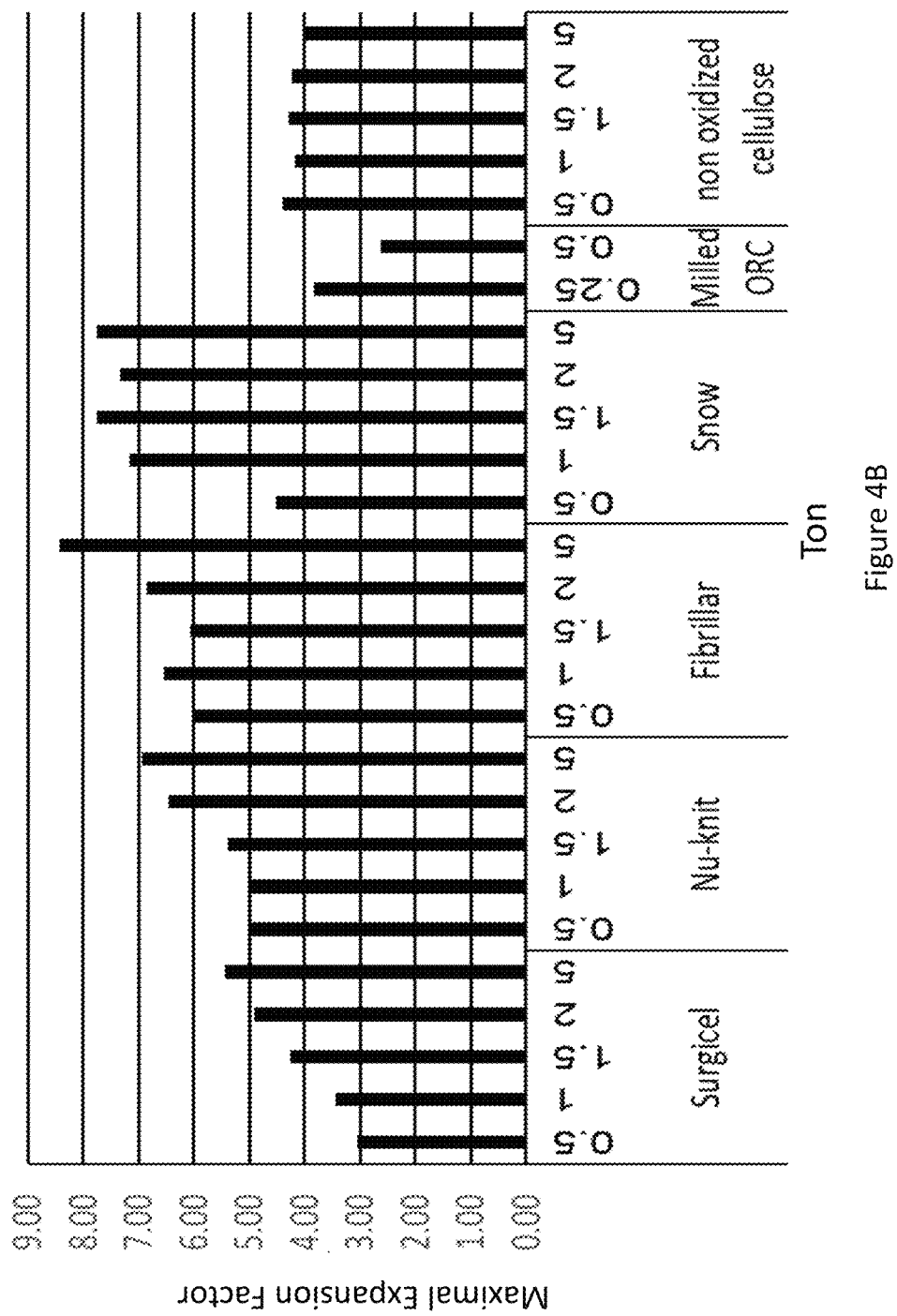
Figure 4C:
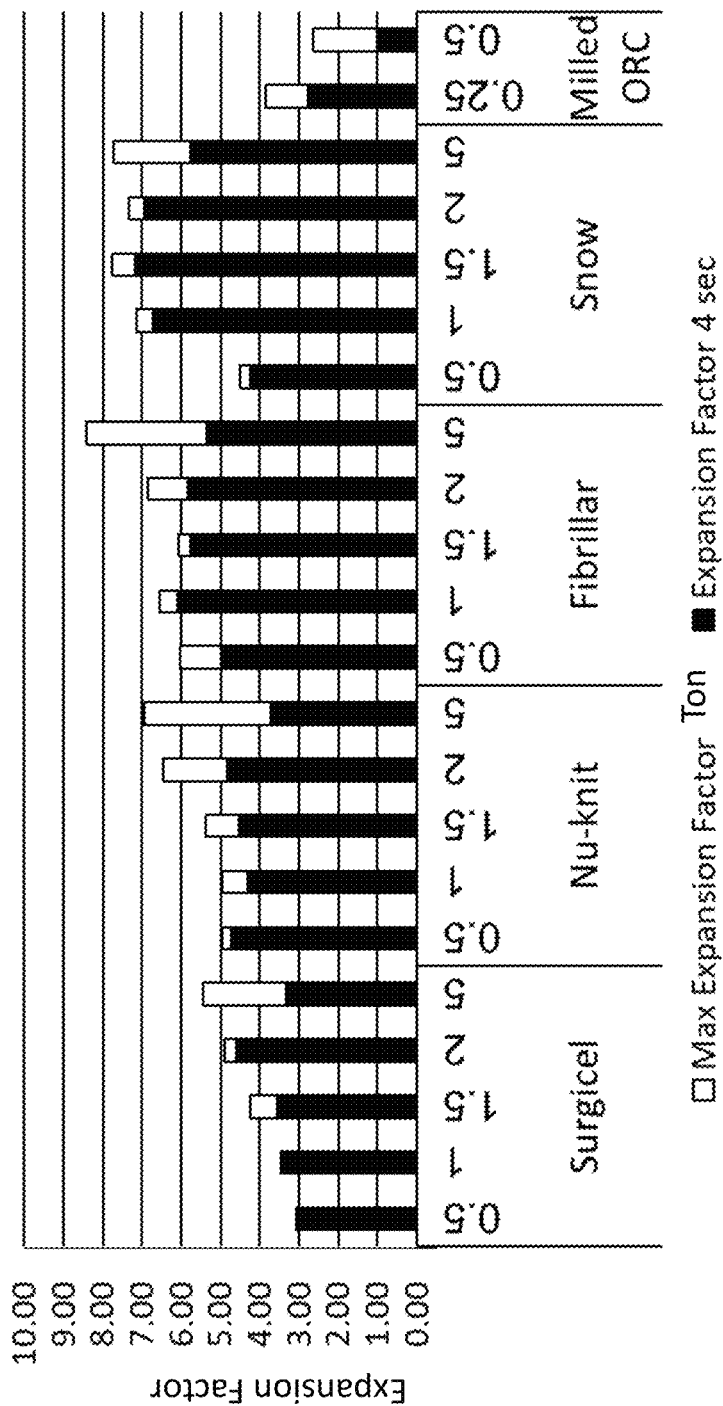
Figure 5:
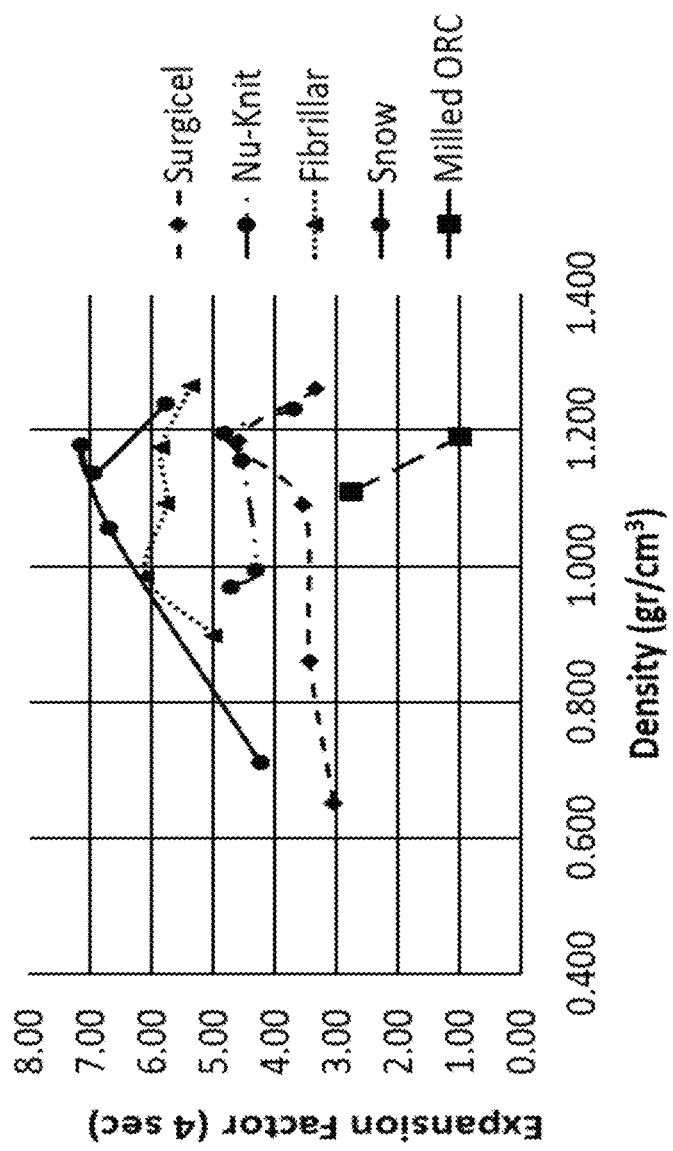
FIG. 5 presents a graph showing the ORC materials density vs. the expansion factor after 4 sec in saline.

The results presented in Table 2B which are further illustrated in FIGS. 4A-5 demonstrate that an ORC density of about 0.8 to 1.2 gr/cm$^3$, and particularly, 0.95 to 1.2 gr/cm$^3$ provides optimal expansion after 4 sec, with the "FIBRILLAR" and "SNoW" exhibiting the highest expansion factor. For comparison, Gauze Pad (non-oxidized cellulose) was also tested, showing poorer expansion factors for certain density values compared to oxidized cellulose samples.

TABLE 2B

| Mater. | Pressure (ton) per 0.785 cm$^2$* | Disc Weight (g) | Disc Height (h) (cm) | Disc Diameter (cm) | Disc surface area (cm$^2$)** | Disc Volume (cm$^3$) | Density (gr/cm$^3$) | Expansion Factor at 4 sec | Max Expansion Factor |
|---|---|---|---|---|---|---|---|---|---|
| 1 | 0.5 | 0.5182 | 0.9215 | 1.0494 | 4.7653 | 0.7966 | 0.651 | 3.06 | 3.06 |
| | 1 | 0.5160 | 0.7042 | 1.0421 | 4.0093 | 0.6003 | 0.860 | 3.45 | 3.45 |
| | 1.5 | 0.5123 | 0.5763 | 1.0195 | 3.4767 | 0.4702 | 1.089 | 3.55 | 4.25 |
| | 2 | 0.5139 | 0.5373 | 1.0147 | 3.3287 | 0.4343 | 1.183 | 4.59 | 4.90 |
| | 5 | 0.5173 | 0.5125 | 1.0098 | 3.2259 | 0.4102 | 1.260 | 3.33 | 5.44 |
| 2 | 0.5 | 0.5135 | 0.6485 | 1.0207 | 3.7142 | 0.5304 | 0.969 | 4.72 | 4.97 |
| | 1 | 0.5145 | 0.6258 | 1.0276 | 3.6772 | 0.5188 | 0.993 | 4.31 | 4.96 |
| | 1.5 | 0.5083 | 0.5446 | 1.0142 | 3.3494 | 0.4398 | 1.156 | 4.55 | 5.38 |
| | 2 | 0.5104 | 0.5358 | 1.0075 | 3.2886 | 0.4269 | 1.195 | 4.83 | 6.45 |
| | 5 | 0.5084 | 0.5158 | 1.0101 | 3.2380 | 0.4132 | 1.230 | 3.71 | 6.93 |
| 3 | 0.5 | 0.5062 | 0.6922 | 1.0198 | 3.8490 | 0.5650 | 0.898 | 4.99 | 6.04 |
| | 1 | 0.5164 | 0.6463 | 1.0169 | 3.6873 | 0.5247 | 0.984 | 6.10 | 6.54 |
| | 1.5 | 0.5040 | 0.5718 | 1.0145 | 3.4371 | 0.4619 | 1.091 | 5.77 | 6.05 |
| | 2 | 0.5072 | 0.5396 | 1.0104 | 3.3147 | 0.4324 | 1.173 | 5.85 | 6.86 |
| | 5 | 0.5105 | 0.5081 | 1.0059 | 3.1933 | 0.4036 | 1.264 | 5.37 | 8.42 |
| 4 | 0.5 | 0.5249 | 0.8909 | 1.0278 | 4.5336 | 0.7388 | 0.711 | 4.24 | 4.51 |
| | 1 | 0.5562 | 0.6527 | 1.0136 | 3.6901 | 0.5263 | 1.056 | 6.71 | 7.15 |
| | 1.5 | 0.5365 | 0.5712 | 1.0079 | 3.4025 | 0.4555 | 1.177 | 7.16 | 7.76 |
| | 2 | 0.5221 | 0.5727 | 1.0110 | 3.4228 | 0.4595 | 1.136 | 6.96 | 7.32 |
| | 5 | 0.5277 | 0.5341 | 1.0081 | 3.2865 | 0.4261 | 1.238 | 5.79 | 7.74 |
| 5 | 0.25 | 0.4903 | 0.5552 | 1.0076 | 3.3506 | 0.4425 | 1.107 | 2.79 | 3.84 |
| | 0.5 | 0.4826 | 0.5100 | 1.0063 | 3.2013 | 0.4054 | 1.190 | 1.00 | 2.63 |

TABLE 2B-continued

| Mater. | Pressure (ton) per 0.785 cm²* | Disc Weight (g) | Disc Height (h) (cm) | Disc Diameter (cm) | Disc surface area (cm²)** | Disc Volume (cm³) | Density (gr/cm³) | Expansion Factor at 4 sec | Max Expansion Factor |
|---|---|---|---|---|---|---|---|---|---|
| 6 | 0.5 | 0.5039 | 0.6038 | 1.0098 | 3.515 | 0.484 | 1.042 | 4.07 | 4.41 |
|   | 1   | 0.5015 | 0.5412 | 1.0064 | 3.300 | 0.431 | 1.165 | 3.48 | 4.19 |
|   | 1.5 | 0.4999 | 0.5119 | 1.0040 | 3.194 | 0.405 | 1.234 | 3.45 | 4.28 |
|   | 2   | 0.5101 | 0.5072 | 1.0039 | 3.182 | 0.401 | 1.271 | 3.32 | 4.23 |
|   | 5   | 0.5072 | 0.4847 | 1.0035 | 3.111 | 0.383 | 1.323 | 2.70 | 4.00 |

*Assuming a round 1 cm mold, and the calculation according to $\pi r^2$ gives 0.785 cm².
**Surface area of a cylinder = $2\pi r^2 + 2\pi rh$
Materials: "1" - SURGICEL; "2"- NU-KNIT; "3"- FIBRILLAR; "4" - SNoW; "5" Milled ORC; "6"- Gauze Pad (non-oxidized cellulose)

Figure 6:
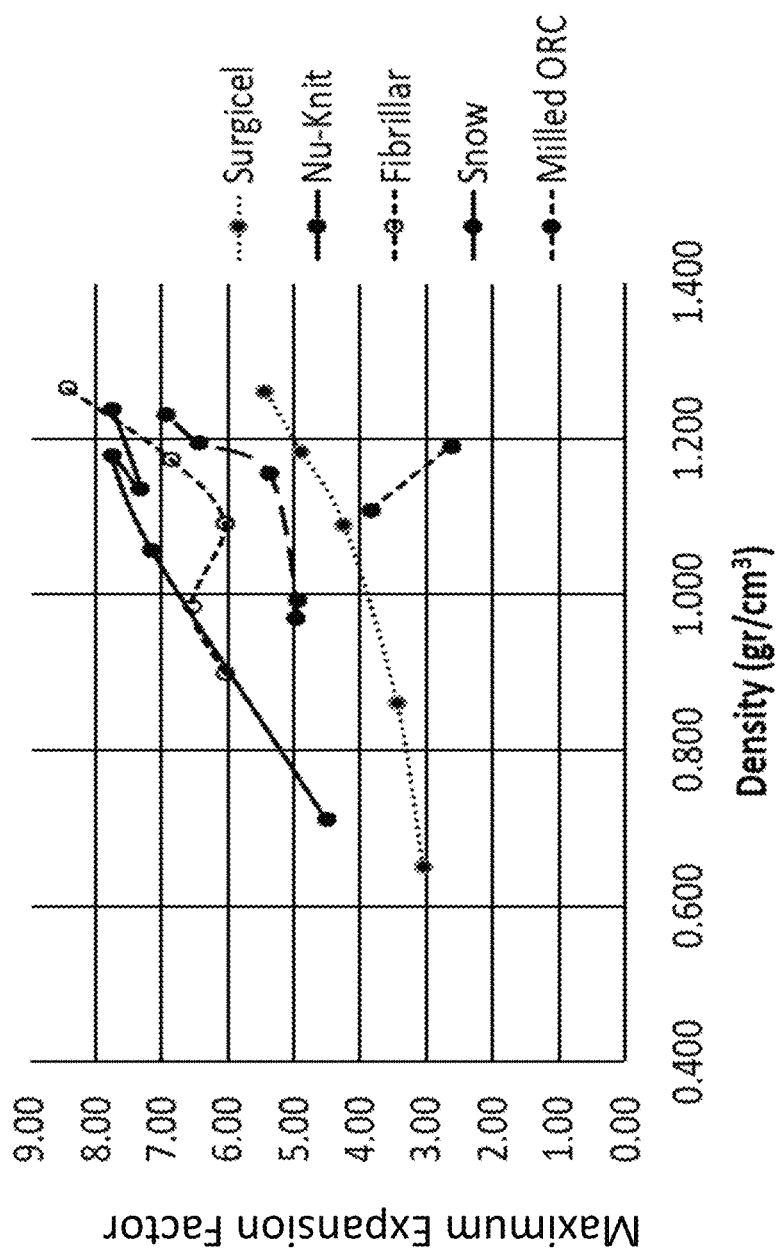
FIG. 6 presents a graph showing the ORC materials density vs. the maximal expansion factor in saline.

FIG. 6 is also based on Table 2B presenting a graph showing the ORC materials density vs. the maximal expansion volume (mL) in saline.

Example 2: In Vivo Study: Porcine Splenic Biopsy Punch Model

For the in-vivo study, the difference hemostatic efficacy of representative tablets composed from the different fabrics (knitted and non-woven) was studied.

For this study a similar expansion time is recommended. Therefore, from the knitted materials material A (see Table 2A) was chosen and from the non-woven materials material C (see Table 2A) was chosen. As described above, both reached their maximum expansion at the same time (8 sec at 2-ton compression) (see FIG. 3B). The 2-ton compression was chosen given its combined results in expansion volume and time of expansion (see FIGS. 3A and 3B).

Materials

ORC material C or ORC material A (5 g of each) compressed into a 0.4 mL (cm³) tablet by applying a 2-ton compression force.

Methods

Porcine Splenic Biopsy Punch model: A mature, about 60 kg, female porcine was put on a fast for 24 hours prior to the surgical procedure. The animal was anesthetized with 1150-1400 mg Ketamine, 115-140 mg Xylazine, 7.5 mg Midazolam. Anesthesia was maintained with Isoflurane and the abdomen was opened to reveal the spleen.

Mean arterial blood pressure, body temperature and heart rate were continuously monitored throughout the surgical procedure. The experiment was terminated when mean arterial blood pressure dropped below 60 mmHg.

Figure 7:
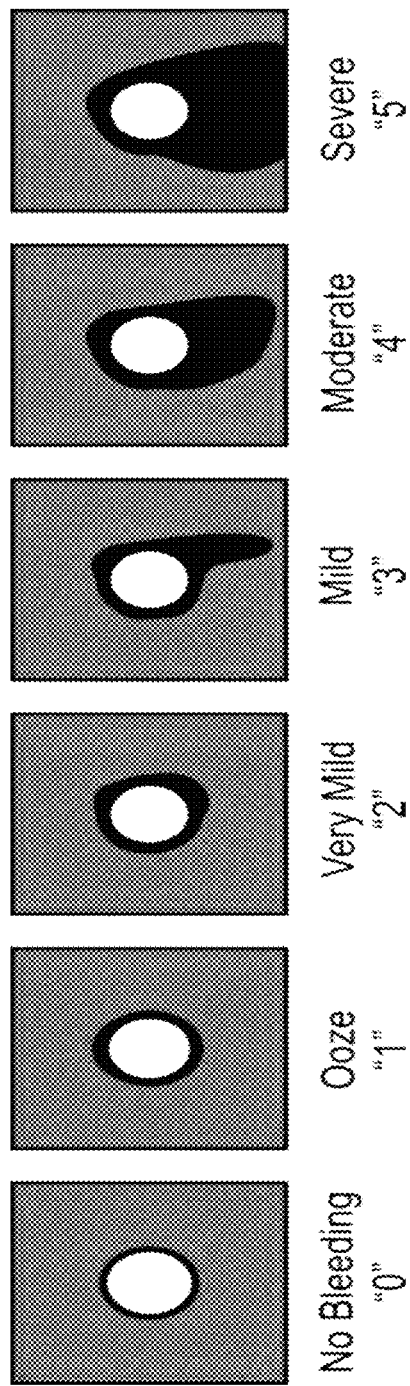
FIG. 7 presents images showing a schematic illustration of bleeding levels grade used in the spleen biopsy punch model. The white circle represents the punch, the grey circle represents background the tissue and the black circle represents the blood flowing from the biopsy punch site (from left panel to right: No Bleeding "0"; Ooze "1"; Very Mild "2"; Mild "3"; Moderate "4"; Severe "5").

An 8 mm diameter×3 mm depth biopsy punch was carried out on the spleen and the specimen was excised with surgical scissors. The punch site was allowed to bleed for 30 seconds and bleeding intensity was visually assessed on a scale of 0-5 (as described in FIG. 7); "no bleeding" was given a score of 0 and "intensive bleeding" was given a score of 5. Next, the punch site was wiped with clean gauze to remove excess blood and a single tablet was inserted into the puncture wound. Thereafter, the bleeding rate was re-evaluated according to the scheme describes in FIG. 7.

The results are summarized in Table 3 below showing the effect of ORC tablet application on bleeding levels in an 8 mm diameter×3 mm depth spleen biopsy punch model.

TABLE 3

| Tablet (0.4 cm³, 2T) | Pre-treatment bleeding level (Spleen) | Post treatment bleeding level (Spleen) | Δ bleeding reduction |
|---|---|---|---|
| ORC material A | 3 | 1 | 2 |
| Non-compressed ORC material C | 4 | 2 | 2 |
| ORC material C | 4 | 1 | 3 |

Application of tablet of ORC material A to a puncture with a graded bleeding level of 3 ("mild" bleeding) resulted in bleeding reduction to a grade 1 level ("ooze"). Application of the ORC material C tablet exhibited superior efficacy and was able to reduce a 4-grade bleeding level ("moderate" bleeding) down to 1 ("ooze"). During application it was shown that the ORC material C tablet expanded much more rapidly and was able to reduce the bleeding at higher efficacy and at a faster rate than the tablet of ORC material A. These results show that the textured of the properties of the non-woven compressed fabric that expand to greater volume and at a faster rate than the compressed knitted ORC, also exhibits improved efficacy in hemostasis of puncture bleeding. Application of a non-compressed ORC material C exhibited reduced efficacy—decrease of bleeding level from 4 ("moderate") to 2 ("mild")—suggesting an advantage of the compressed tablet in immediate hemostasis of puncture wounds over the non-compressed material.

Example 3: In Vivo Study: Heparinized Porcine Splenic Biopsy Punch Model

A mature, about 60 kg, female porcine was treated as described above, with abdomen being opened to reveal the liver or spleen, and with 27,000 IU of Heparin being administered prior to biopsy procedure. ACT (Activated Clotting Time) test was used in order to monitor the Heparin treatment. Accordingly, Heparin boosts were given in order to maintain stable ACT levels. Heparin is used as an injectable anticoagulant (through antithrombin III activation) and therefore this model represents a challenging bleeding model.

The liver was subjected to 8 mm diameter×3 mm depth biopsy punch. The Porcine spleen was subjected to 6 mm diameter×3 mm depth biopsy punch. In both organs, the specimen was excised with surgical scissors. The punch site was allowed to bleed for 30 seconds and bleeding intensity (level) was visually assessed on a scale of 0-5, as described above. The results are summarized in Table 4 showing the effect of ORC tablet application on bleeding levels in an 8 mm diameter×3 mm depth liver biopsy punch model, and in Table 5 showing the effect of ORC tablet application on the bleeding level in a 6 mm diameter×3 mm depth spleen biopsy punch model. The hemostatic efficacy evaluation was performed in the porcine liver and in the porcine spleen. The ORC tablets were manually applied to the wound sites.

TABLE 4

| Tablet (0.4 cm³, 2T) | Pre-Treatment Bleeding Level (Liver) | Post Treatment Bleeding Level (Liver) | Δ bleeding reduction |
|---|---|---|---|
| ORC material C (Fibrillar)* | 4 | 0 | 4 |
| ORC material D (SNoW) | 4 | 0 | 4 |
| ORC short (milled ORC) | 4 | 4 | 0 |

*Triplicate

TABLE 5

| Tablet (0.4 cm³, 2T) | Pre-Treatment Bleeding Level (Spleen) | Post Treatment Bleeding Level (Spleen) | Δ Bleeding Reduction |
|---|---|---|---|
| ORC material C | 3 | 0 | 3 |
| ORC material D | 2 | 0 | 2 |
| ORC material D | 4 | 0 | 4 |
| ORC short | 3 | 2 | 1 |
| ORC short | 4 | 3 | 1 |
| ORC short | 4 | 2 | 2 |

Application of non-woven ORC tablets (material C-triplicate, material D-monoplicate) to the liver completely stopped the bleeding from a bleeding intensity of 4 to 0 (from "moderate" to "no bleeding") in an 8 mm diameter×3 mm depth biopsy punch size (as shown in Table 4). Application of compressed tablets of "ORC short" showed almost no expansion of the tablet and the sample failed to achieve hemostasis (as shown in Table 4).

Application of non-woven ORC tablets (material C-monoplicate, material D-duplicate) to the porcine spleen completely stopped the bleeding from a bleeding intensity of 2/3/4 (the initial bleeding level) to 0 (as shown in Table 5). Application of compressed tablet of "ORC short" (triplicate was tested) showed bleeding reduction of 1 or 2.

The results show that compressed tablets produced from non-woven ORC materials exhibit higher efficacy over tablets produced from other ORC materials. These tablets can be potentially applied in new surgical scenarios and broaden the application scope for ORC-based material.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A biodegradable hemostatic matrix comprising oxidized regenerated cellulose (ORC), wherein said ORC is in the form of a non-woven fabric, said ORC comprising sheets, wherein the sheets are fibrous and packed layered sheets, and wherein said matrix is a compressed tablet or pellet having a density ranging from 0.95 to 1.2 gr/cm³, and wherein said compressed tablet or pellet is expandable to at least 3 times its original volume within 4 sec upon contact with an aqueous solution at at-least one temperature between 1 and 40° C.

2. The matrix of claim 1, being capable of expanding to at least 90% of its maximum expansion capacity within 30 seconds following immersion in an aqueous solution.

3. The matrix of claim 2, being expandable to 15 to 30 times its original volume within 4 sec upon contact with an aqueous solution at at-least one temperature between 10 and 30° C.

4. The matrix of claim 1, further comprising one or more additives selected from the group consisting of calcium salt, anti-infective agent, and hemostasis promoting agent.

5. The matrix of claim 1, further comprising one or more excipients selected from the group consisting of sodium chloride, mannitol, albumin, and sodium acetate.

6. The matrix of claim 1, wherein the carboxyl content of the ORC ranges from 12% to 21%, by weight, per United States Pharmacopeia (USP) 23-NF18.

7. The matrix of claim 1, having a pre-expansion total surface area ranging from about 0.5 to about 10 cm².

8. The matrix of claim 1, produced by compressing an ORC-based material by applying on a surface thereof a pressure ranging from 0.3 to 7 ton/cm².

9. The matrix of claim 1, wherein the ORC comprises less than 8% water prior to the contact with the aqueous solution.

10. The matrix of claim 1, being expandable to at least 4 times its original volume within 4 sec upon contact with an aqueous solution at at-least one temperature between 10 and 40° C.

11. The matrix of claim 1, being expandable to at least 5 times its original volume within 4 sec upon contact with an aqueous solution at at-least one temperature between 10 and 40° C.

12. The matrix of claim 1, being expandable to 3 to 6 times its original volume within 4 sec upon contact with an aqueous solution at at-least one temperature between 10 and 40° C.

13. A method of treating a wound comprising the step of applying the biodegradable hemostatic matrix of claim 1 onto and/or into the wound of a subject in a need thereof.

* * * * *